(12) United States Patent
Wescott et al.

(10) Patent No.: US 7,041,790 B2
(45) Date of Patent: May 9, 2006

(54) FIBRINOGEN BINDING MOIETIES

(75) Inventors: Charles R. Wescott, Belmont, MA (US); Aaron K. Sato, Somerville, MA (US)

(73) Assignee: Dyax Corp., Cambridge, MA (US)

( * ) Notice: Subject to any disclaimer, the term of this patent is extended or adjusted under 35 U.S.C. 154(b) by 447 days.

(21) Appl. No.: 10/396,073

(22) Filed: Mar. 25, 2003

(65) Prior Publication Data

US 2003/0207330 A1   Nov. 6, 2003

Related U.S. Application Data

(60) Provisional application No. 60/367,645, filed on Mar. 26, 2002.

(51) Int. Cl.
*A61K 38/00* (2006.01)
*A61K 35/14* (2006.01)

(52) U.S. Cl. .................. 530/328; 530/327; 530/326; 530/325; 530/324; 530/380; 514/2

(58) Field of Classification Search ........ 530/324–328, 530/382; 514/2
See application file for complete search history.

(56) References Cited

U.S. PATENT DOCUMENTS 5,116,944 A   5/1992   Sivam et al.

FOREIGN PATENT DOCUMENTS

| EP | 0 395 918 A2 | 11/1990 |
| WO | WO 91/01743 | 2/1991 |
| WO | WO 97/30734 | 8/1997 |

OTHER PUBLICATIONS

Russell et al., "Crystal structure studies on fibrinogen and fibrin," Ann. N.Y. Acad. Sci., 2001; 936(1); pp. 31-43.
International Search Report for PCT/US03/08732 mailed Nov. 4, 2004.

*Primary Examiner*—Jon Weber
*Assistant Examiner*—Suzanne M. (Mayer) Noakes
(74) *Attorney, Agent, or Firm*—Fish & Richardson P.C.

(57) ABSTRACT

Compositions comprising non-naturally occurring fibrinogen binding moieties are described, together with methods of use thereof, e.g., for detecting or isolating fibrinogen molecules in a solution, for blood circulation imaging, and for linking therapeutics or other molecules to fibrinogen. Preferred binding peptides having a high affinity for fibrinogen are particularly disclosed.

23 Claims, 5 Drawing Sheets

A   B   C   D

SEQUENCE LISTING

```
<160> NUMBER OF SEQ ID NOS: 48

<210> SEQ ID NO 1
<211> LENGTH: 4
<212> TYPE: PRT
<213> ORGANISM: artificial
<220> FEATURE:
<223> OTHER INFORMATION: N-terminal peptide of fibrinogen alpha chain

<400> SEQUENCE: 1

Gly Pro Arg Val
1

<210> SEQ ID NO 2
<211> LENGTH: 12
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (1)..(1)
<223> OTHER INFORMATION: X1 is His or Tyr
<220> FEATURE:
<221> NAME/KEY: MISC_FEATURE
<222> LOCATION: (5)..(5)
<223> OTHER INFORMATION: X5 is Asp or Thr
<220> FEATURE:
<221> NAME/KEY: MISC_FEATURE
<222> LOCATION: (6)..(6)
<223> OTHER INFORMATION: X6 is Ser or Trp
<220> FEATURE:
<221> NAME/KEY: MISC_FEATURE
<222> LOCATION: (7)..(7)
<223> OTHER INFORMATION: X7 is His or Trp
<220> FEATURE:
<221> NAME/KEY: MISC_FEATURE
<222> LOCATION: (8)..(8)
<223> OTHER INFORMATION: X8 is Gly or His
<220> FEATURE:
<221> NAME/KEY: MISC_FEATURE
<222> LOCATION: (10)..(10)
<223> OTHER INFORMATION: X10 is Gly or Val
<220> FEATURE:
<221> NAME/KEY: MISC_FEATURE
<222> LOCATION: (11)..(11)
<223> OTHER INFORMATION: X11 is His or Val
<220> FEATURE:
<221> NAME/KEY: MISC_FEATURE
<222> LOCATION: (12)..(12)
```

<223> OTHER INFORMATION: X12 is Phe or Trp

<400> SEQUENCE: 2

Xaa Trp Tyr Cys Xaa Xaa Xaa Xaa Cys Xaa Xaa Xaa
1               5                   10

<210> SEQ ID NO 3
<211> LENGTH: 6
<212> TYPE: PRT
<213> ORGANISM: artificial
<220> FEATURE:
<223> OTHER INFORMATION: fibrinogen binding peptide
<220> FEATURE:
<221> NAME/KEY: MISC_FEATURE
<222> LOCATION: (2)..(2)
<223> OTHER INFORMATION: X2 is Asp or Thr
<220> FEATURE:
<221> NAME/KEY: MISC_FEATURE
<222> LOCATION: (3)..(3)
<223> OTHER INFORMATION: X3 is Ser or Trp
<220> FEATURE:
<221> NAME/KEY: MISC_FEATURE
<222> LOCATION: (4)..(4)
<223> OTHER INFORMATION: X4 is His or Trp
<220> FEATURE:
<221> NAME/KEY: MISC_FEATURE
<222> LOCATION: (5)..(5)
<223> OTHER INFORMATION: X5 is Gly or His

<400> SEQUENCE: 3

Cys Xaa Xaa Xaa Xaa Cys
1               5

<210> SEQ ID NO 4
<211> LENGTH: 16
<212> TYPE: PRT
<213> ORGANISM: artificial
<220> FEATURE:
<223> OTHER INFORMATION: fibrinogen binding polypeptide

<400> SEQUENCE: 4

Gly Ser Tyr Trp Tyr Cys Asp Ser Trp His Cys Gly Val Phe Ala Pro
1               5                   10                  15

<210> SEQ ID NO 5
<211> LENGTH: 16
<212> TYPE: PRT
<213> ORGANISM: artificial
<220> FEATURE:
<223> OTHER INFORMATION: fibrinogen binding polypeptide

<400> SEQUENCE: 5

Gly Ser His Trp Tyr Cys Thr Trp His Gly Cys Val His Trp Ala Pro
1               5                   10                  15

<210> SEQ ID NO 6
<211> LENGTH: 13
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (1)..(1)
<223> OTHER INFORMATION: X1 is Asp or Leu
<220> FEATURE:
<221> NAME/KEY: MISC_FEATURE
<222> LOCATION: (2)..(2)
<223> OTHER INFORMATION: X2 is Gly or Pro
<220> FEATURE:
<221> NAME/KEY: MISC_FEATURE

```
<222> LOCATION: (3)..(3)
<223> OTHER INFORMATION: X3 is Gln or Trp
<220> FEATURE:
<221> NAME/KEY: MISC_FEATURE
<222> LOCATION: (5)..(5)
<223> OTHER INFORMATION: X5 is Glu or Lys
<220> FEATURE:
<221> NAME/KEY: MISC_FEATURE
<222> LOCATION: (6)..(6)
<223> OTHER INFORMATION: X6 is Met or Pro
<220> FEATURE:
<221> NAME/KEY: MISC_FEATURE
<222> LOCATION: (7)..(7)
<223> OTHER INFORMATION: X7 is Pro or Tyr
<220> FEATURE:
<221> NAME/KEY: MISC_FEATURE
<222> LOCATION: (8)..(8)
<223> OTHER INFORMATION: X8 is Gly or Leu
<220> FEATURE:
<221> NAME/KEY: MISC_FEATURE
<222> LOCATION: (9)..(9)
<223> OTHER INFORMATION: X9 is Thr or Trp
<220> FEATURE:
<221> NAME/KEY: MISC_FEATURE
<222> LOCATION: (12)..(12)
<223> OTHER INFORMATION: X12 is Gln or Thr
<220> FEATURE:
<221> NAME/KEY: MISC_FEATURE
<222> LOCATION: (13)..(13)
<223> OTHER INFORMATION: X13 is Leu or Tyr

<400> SEQUENCE: 6

Xaa Xaa Xaa Cys Xaa Xaa Xaa Xaa Xaa Cys Trp Xaa Xaa
1               5                   10

<210> SEQ ID NO 7
<211> LENGTH: 7
<212> TYPE: PRT
<213> ORGANISM: artificial
<220> FEATURE:
<223> OTHER INFORMATION: fibrinogen binding peptide
<220> FEATURE:
<221> NAME/KEY: MISC_FEATURE
<222> LOCATION: (2)..(2)
<223> OTHER INFORMATION: X2 is Glu or Lys
<220> FEATURE:
<221> NAME/KEY: MISC_FEATURE
<222> LOCATION: (3)..(3)
<223> OTHER INFORMATION: X3 is Met or Pro
<220> FEATURE:
<221> NAME/KEY: MISC_FEATURE
<222> LOCATION: (4)..(4)
<223> OTHER INFORMATION: X4 is Pro or Tyr
<220> FEATURE:
<221> NAME/KEY: MISC_FEATURE
<222> LOCATION: (5)..(5)
<223> OTHER INFORMATION: X5 is Gly or Leu
<220> FEATURE:
<221> NAME/KEY: MISC_FEATURE
<222> LOCATION: (6)..(6)
<223> OTHER INFORMATION: X6 is Thr or Trp

<400> SEQUENCE: 7

Cys Xaa Xaa Xaa Xaa Xaa Cys
1               5

<210> SEQ ID NO 8
<211> LENGTH: 17
<212> TYPE: PRT
<213> ORGANISM: artificial
<220> FEATURE:
<223> OTHER INFORMATION: fibrinogen binding polypeptide

<400> SEQUENCE: 8
```

```
Ala Gly Leu Pro Gln Cys Glu Met Tyr Gly Thr Cys Trp Thr Tyr Gly
1               5                   10                  15
Thr
```

<210> SEQ ID NO 9
<211> LENGTH: 17
<212> TYPE: PRT
<213> ORGANISM: artificial
<220> FEATURE:
<223> OTHER INFORMATION: fibrinogen binding polypeptide

<400> SEQUENCE: 9

```
Ala Gly Asp Gly Trp Cys Lys Pro Pro Leu Trp Cys Trp Gln Leu Gly
1               5                   10                  15
Thr
```

<210> SEQ ID NO 10
<211> LENGTH: 14
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (1)..(1)
<223> OTHER INFORMATION: X1 is Trp, Tyr or Val
<220> FEATURE:
<221> NAME/KEY: MISC_FEATURE
<222> LOCATION: (2)..(2)
<223> OTHER INFORMATION: X2 is Pro, Trp, or Val
<220> FEATURE:
<221> NAME/KEY: MISC_FEATURE
<222> LOCATION: (3)..(3)
<223> OTHER INFORMATION: X3 is Pro, Ser, or Trp
<220> FEATURE:
<221> NAME/KEY: MISC_FEATURE
<222> LOCATION: (5)..(5)
<223> OTHER INFORMATION: X5 is Ala, Asp, or Met
<220> FEATURE:
<221> NAME/KEY: MISC_FEATURE
<222> LOCATION: (6)..(6)
<223> OTHER INFORMATION: X6 is Pro or Val, preferably Val
<220> FEATURE:
<221> NAME/KEY: MISC_FEATURE
<222> LOCATION: (7)..(7)
<223> OTHER INFORMATION: X7 is Met, Thr, or Trp
<220> FEATURE:
<221> NAME/KEY: MISC_FEATURE
<222> LOCATION: (8)..(8)
<223> OTHER INFORMATION: Xaa8 is Asp, Gly, or Trp
<220> FEATURE:
<221> NAME/KEY: MISC_FEATURE
<222> LOCATION: (9)..(9)
<223> OTHER INFORMATION: X9 is Glu, Leu, or Met
<220> FEATURE:
<221> NAME/KEY: MISC_FEATURE
<222> LOCATION: (10)..(10)
<223> OTHER INFORMATION: X10 is Gln, Trp, or Tyr
<220> FEATURE:
<221> NAME/KEY: MISC_FEATURE
<222> LOCATION: (12)..(12)
<223> OTHER INFORMATION: X12 is Pro, Trp, or Val
<220> FEATURE:
<221> NAME/KEY: MISC_FEATURE
<222> LOCATION: (13)..(13)
<223> OTHER INFORMATION: X13 is Ser, Thr, or Trp
<220> FEATURE:
<221> NAME/KEY: MISC_FEATURE
<222> LOCATION: (14)..(14)
<223> OTHER INFORMATION: X14 is Arg, Asn, or Thr

<400> SEQUENCE: 10

Xaa Xaa Xaa Cys Xaa Xaa Xaa Xaa Xaa Xaa Cys Xaa Xaa Xaa

```
<210> SEQ ID NO 11
<211> LENGTH: 8
<212> TYPE: PRT
<213> ORGANISM: artificial
<220> FEATURE:
<223> OTHER INFORMATION: fibrinogen binding peptide
<220> FEATURE:
<221> NAME/KEY: MISC_FEATURE
<222> LOCATION: (2)..(2)
<223> OTHER INFORMATION: X2 is Ala, Asp, or Met
<220> FEATURE:
<221> NAME/KEY: MISC_FEATURE
<222> LOCATION: (3)..(3)
<223> OTHER INFORMATION: X3 is Pro or Val, preferably Val
<220> FEATURE:
<221> NAME/KEY: MISC_FEATURE
<222> LOCATION: (4)..(4)
<223> OTHER INFORMATION: X4 is Met, Thr, or Trp
<220> FEATURE:
<221> NAME/KEY: MISC_FEATURE
<222> LOCATION: (5)..(5)
<223> OTHER INFORMATION: X5 is Asp, Gly, or Trp
<220> FEATURE:
<221> NAME/KEY: MISC_FEATURE
<222> LOCATION: (6)..(6)
<223> OTHER INFORMATION: X6 is Glu, Leu, or Met
<220> FEATURE:
<221> NAME/KEY: MISC_FEATURE
<222> LOCATION: (7)..(7)
<223> OTHER INFORMATION: X7 is Gln, Trp, or Tyr

<400> SEQUENCE: 11

Cys Xaa Xaa Xaa Xaa Xaa Xaa Cys
1               5

<210> SEQ ID NO 12
<211> LENGTH: 18
<212> TYPE: PRT
<213> ORGANISM: artificial
<220> FEATURE:
<223> OTHER INFORMATION: fibrinogen binding polypeptide

<400> SEQUENCE: 12

Ala Gly Tyr Trp Trp Cys Ala Val Trp Gly Glu Gln Cys Val Thr Arg
1               5                   10                  15

Gly Thr

<210> SEQ ID NO 13
<211> LENGTH: 18
<212> TYPE: PRT
<213> ORGANISM: artificial
<220> FEATURE:
<223> OTHER INFORMATION: fibrinogen binding polypeptide

<400> SEQUENCE: 13

Ala Gly Val Pro Ser Cys Met Val Met Asp Met Trp Cys Pro Trp Asn
1               5                   10                  15

Gly Thr

<210> SEQ ID NO 14
<211> LENGTH: 18
<212> TYPE: PRT
<213> ORGANISM: artificial
<220> FEATURE:
<223> OTHER INFORMATION: fibrinogen binding polypeptide

<400> SEQUENCE: 14
```

```
Ala Gly Trp Val Pro Cys Asp Pro Thr Trp Leu Tyr Cys Trp Ser Thr
1               5                   10                  15

Gly Thr

<210> SEQ ID NO 15
<211> LENGTH: 15
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (1)..(1)
<223> OTHER INFORMATION: X1 is Pro or Trp, preferably Pro
<220> FEATURE:
<221> NAME/KEY: MISC_FEATURE
<222> LOCATION: (2)..(2)
<223> OTHER INFORMATION: X2 is Asn or Leu, preferably Leu
<220> FEATURE:
<221> NAME/KEY: MISC_FEATURE
<222> LOCATION: (3)..(3)
<223> OTHER INFORMATION: X3 is His, Pro, or Val
<220> FEATURE:
<221> NAME/KEY: MISC_FEATURE
<222> LOCATION: (5)..(5)
<223> OTHER INFORMATION: X5 is Ala, His, or Val
<220> FEATURE:
<221> NAME/KEY: MISC_FEATURE
<222> LOCATION: (6)..(6)
<223> OTHER INFORMATION: X6 is Ala, Asp, or Glu
<220> FEATURE:
<221> NAME/KEY: MISC_FEATURE
<222> LOCATION: (7)..(7)
<223> OTHER INFORMATION: X7 is Ala, Asn, or Ser
<220> FEATURE:
<221> NAME/KEY: MISC_FEATURE
<222> LOCATION: (8)..(8)
<223> OTHER INFORMATION: X8 is Arg, Pro, or Tyr
<220> FEATURE:
<221> NAME/KEY: MISC_FEATURE
<222> LOCATION: (9)..(9)
<223> OTHER INFORMATION: X9 is Asn, Lys, or Trp
<220> FEATURE:
<221> NAME/KEY: MISC_FEATURE
<222> LOCATION: (10)..(10)
<223> OTHER INFORMATION: X10 is Leu, Pro, or Tyr
<220> FEATURE:
<221> NAME/KEY: MISC_FEATURE
<222> LOCATION: (11)..(11)
<223> OTHER INFORMATION: X11 is Gly, His, or Leu
<220> FEATURE:
<221> NAME/KEY: MISC_FEATURE
<222> LOCATION: (13)..(13)
<223> OTHER INFORMATION: X13 is Ile, Phe, or Trp
<220> FEATURE:
<221> NAME/KEY: MISC_FEATURE
<222> LOCATION: (14)..(14)
<223> OTHER INFORMATION: X14 is His, Phe, or Val
<220> FEATURE:
<221> NAME/KEY: MISC_FEATURE
<222> LOCATION: (15)..(15)
<223> OTHER INFORMATION: X15 is Gly, Leu, or Ser

<400> SEQUENCE: 15

Xaa Xaa Xaa Cys Xaa Xaa Xaa Xaa Xaa Xaa Xaa Cys Xaa Xaa Xaa
1               5                   10                  15

<210> SEQ ID NO 16
<211> LENGTH: 9
<212> TYPE: PRT
<213> ORGANISM: artificial
<220> FEATURE:
<223> OTHER INFORMATION: fibrinogen binding peptide
<220> FEATURE:
<221> NAME/KEY: MISC_FEATURE
```

```
<222> LOCATION: (2)..(2)
<223> OTHER INFORMATION: X2 is Ala, His, or Val
<220> FEATURE:
<221> NAME/KEY: MISC_FEATURE
<222> LOCATION: (3)..(3)
<223> OTHER INFORMATION: X3 is Ala, Asp, or Glu
<220> FEATURE:
<221> NAME/KEY: MISC_FEATURE
<222> LOCATION: (4)..(4)
<223> OTHER INFORMATION: X4 is Ala, Asn, or Ser
<220> FEATURE:
<221> NAME/KEY: MISC_FEATURE
<222> LOCATION: (5)..(5)
<223> OTHER INFORMATION: X5 is Arg, Pro, or Tyr
<220> FEATURE:
<221> NAME/KEY: MISC_FEATURE
<222> LOCATION: (6)..(6)
<223> OTHER INFORMATION: X6 is Asn, Lys, or Trp
<220> FEATURE:
<221> NAME/KEY: MISC_FEATURE
<222> LOCATION: (7)..(7)
<223> OTHER INFORMATION: X7 is Leu, Pro, or Tyr
<220> FEATURE:
<221> NAME/KEY: MISC_FEATURE
<222> LOCATION: (8)..(8)
<223> OTHER INFORMATION: X8 is Gly, His, or Leu

<400> SEQUENCE: 16

Cys Xaa Xaa Xaa Xaa Xaa Xaa Cys
1               5

<210> SEQ ID NO 17
<211> LENGTH: 19
<212> TYPE: PRT
<213> ORGANISM: artificial
<220> FEATURE:
<223> OTHER INFORMATION: fibrinogen binding polypeptide

<400> SEQUENCE: 17

Ala Gly Trp Leu Pro Cys Ala Asp Asn Arg Trp Leu Leu Cys Phe Phe
1               5                   10                  15

Gly Gly Thr

<210> SEQ ID NO 18
<211> LENGTH: 19
<212> TYPE: PRT
<213> ORGANISM: artificial
<220> FEATURE:
<223> OTHER INFORMATION: fibrinogen binding polypeptide

<400> SEQUENCE: 18

Ala Gly Pro Leu Val Cys Val Glu Ser Pro Asn Tyr His Cys Ile Val
1               5                   10                  15

Leu Gly Thr

<210> SEQ ID NO 19
<211> LENGTH: 19
<212> TYPE: PRT
<213> ORGANISM: artificial
<220> FEATURE:
<223> OTHER INFORMATION: fibrinogen binding polypeptide

<400> SEQUENCE: 19

Ala Gly Pro Asn His Cys His Ala Ala Tyr Lys Pro Gly Cys Trp His
1               5                   10                  15

Ser Gly Thr

<210> SEQ ID NO 20
```

```
<211> LENGTH: 16
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (1)..(1)
<223> OTHER INFORMATION: X1 is His, Leu, or Phe
<220> FEATURE:
<221> NAME/KEY: MISC_FEATURE
<222> LOCATION: (2)..(2)
<223> OTHER INFORMATION: X2 is Asp, Trp, or Tyr
<220> FEATURE:
<221> NAME/KEY: MISC_FEATURE
<222> LOCATION: (3)..(3)
<223> OTHER INFORMATION: X3 is Leu or Tyr, preferably Leu
<220> FEATURE:
<221> NAME/KEY: MISC_FEATURE
<222> LOCATION: (5)..(5)
<223> OTHER INFORMATION: X5 is Asn, Met, or Ser
<220> FEATURE:
<221> NAME/KEY: MISC_FEATURE
<222> LOCATION: (6)..(6)
<223> OTHER INFORMATION: X6 is Ala or Ser
<220> FEATURE:
<221> NAME/KEY: MISC_FEATURE
<222> LOCATION: (7)..(7)
<223> OTHER INFORMATION: X7 is Arg, Asn, or Tyr
<220> FEATURE:
<221> NAME/KEY: MISC_FEATURE
<222> LOCATION: (8)..(8)
<223> OTHER INFORMATION: X8 is Pro, Thr, or Trp
<220> FEATURE:
<221> NAME/KEY: MISC_FEATURE
<222> LOCATION: (9)..(9)
<223> OTHER INFORMATION: X9 is Ile, Met, or Tyr
<220> FEATURE:
<221> NAME/KEY: MISC_FEATURE
<222> LOCATION: (10)..(10)
<223> OTHER INFORMATION: X10 is Ala, His, or Ser
<220> FEATURE:
<221> NAME/KEY: MISC_FEATURE
<222> LOCATION: (11)..(11)
<223> OTHER INFORMATION: X11 is Leu, Pro, or Tyr
<220> FEATURE:
<221> NAME/KEY: MISC_FEATURE
<222> LOCATION: (12)..(12)
<223> OTHER INFORMATION: X12 is Trp or Tyr, preferably Tyr
<220> FEATURE:
<221> NAME/KEY: MISC_FEATURE
<222> LOCATION: (14)..(14)
<223> OTHER INFORMATION: X14 is Asn, His, or Val
<220> FEATURE:
<221> NAME/KEY: MISC_FEATURE
<222> LOCATION: (15)..(15)
<223> OTHER INFORMATION: X15 is Asp, Phe, or Pro
<220> FEATURE:
<221> NAME/KEY: MISC_FEATURE
<222> LOCATION: (16)..(16)
<223> OTHER INFORMATION: X16 is Asn, Phe, or Ser

<400> SEQUENCE: 20

Xaa Xaa Xaa Cys Xaa Xaa Xaa Xaa Xaa Xaa Xaa Xaa Cys Xaa Xaa Xaa
 1               5                  10                  15

<210> SEQ ID NO 21
<211> LENGTH: 10
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (2)..(2)
<223> OTHER INFORMATION: X2 is Asn, Met, or Ser
<220> FEATURE:
```

```
<221> NAME/KEY: MISC_FEATURE
<222> LOCATION: (3)..(3)
<223> OTHER INFORMATION: X3 is Ala or Ser
<220> FEATURE:
<221> NAME/KEY: MISC_FEATURE
<222> LOCATION: (4)..(4)
<223> OTHER INFORMATION: X4 is Arg, Asn, or Tyr
<220> FEATURE:
<221> NAME/KEY: MISC_FEATURE
<222> LOCATION: (5)..(5)
<223> OTHER INFORMATION: X5 is Pro, Thr, or Trp
<220> FEATURE:
<221> NAME/KEY: MISC_FEATURE
<222> LOCATION: (6)..(6)
<223> OTHER INFORMATION: X6 is Ile, Met, or Tyr
<220> FEATURE:
<221> NAME/KEY: MISC_FEATURE
<222> LOCATION: (7)..(7)
<223> OTHER INFORMATION: X7 is Ala, His, or Ser
<220> FEATURE:
<221> NAME/KEY: MISC_FEATURE
<222> LOCATION: (8)..(8)
<223> OTHER INFORMATION: X8 is Leu, Pro, or Tyr
<220> FEATURE:
<221> NAME/KEY: MISC_FEATURE
<222> LOCATION: (9)..(9)
<223> OTHER INFORMATION: X9 is Trp or Tyr

<400> SEQUENCE: 21

Cys Xaa Xaa Xaa Xaa Xaa Xaa Xaa Cys
1               5                   10

<210> SEQ ID NO 22
<211> LENGTH: 20
<212> TYPE: PRT
<213> ORGANISM: artificial
<220> FEATURE:
<223> OTHER INFORMATION: fibrinogen binding polypeptide

<400> SEQUENCE: 22

Gly Ser Leu Tyr Leu Cys Asn Ser Tyr Pro Met His Pro Tyr Cys Asn
1               5                   10                  15

Pro Ser Ala Pro
            20

<210> SEQ ID NO 23
<211> LENGTH: 20
<212> TYPE: PRT
<213> ORGANISM: artificial
<220> FEATURE:
<223> OTHER INFORMATION: fibrinogen binding polypeptide

<400> SEQUENCE: 23

Gly Ser Phe Asp Tyr Cys Ser Ala Asn Thr Tyr Ser Leu Tyr Cys His
1               5                   10                  15

Phe Phe Ala Pro
            20

<210> SEQ ID NO 24
<211> LENGTH: 20
<212> TYPE: PRT
<213> ORGANISM: artificial
<220> FEATURE:
<223> OTHER INFORMATION: fibrinogen binding polypeptide

<400> SEQUENCE: 24

Gly Ser His Trp Leu Cys Met Ser Arg Trp Ile Ala Tyr Trp Cys Val
1               5                   10                  15

Asp Asn Ala Pro
```

20

<210> SEQ ID NO 25
<211> LENGTH: 22
<212> TYPE: PRT
<213> ORGANISM: artificial
<220> FEATURE:
<223> OTHER INFORMATION: fibrinogen binding polypeptide

<400> SEQUENCE: 25

Gly Asp Gly Ser Ser Cys Ser Trp Val Lys Val Gly Trp Leu Trp Glu
1               5                   10                  15

Cys Ala Asp Asp Asp Pro
            20

<210> SEQ ID NO 26
<211> LENGTH: 12
<212> TYPE: PRT
<213> ORGANISM: artificial
<220> FEATURE:
<223> OTHER INFORMATION: fibrinogen binding polypeptide

<400> SEQUENCE: 26

Cys Ser Trp Val Lys Val Gly Trp Leu Trp Glu Cys
1               5                   10

<210> SEQ ID NO 27
<211> LENGTH: 12
<212> TYPE: PRT
<213> ORGANISM: artificial
<220> FEATURE:
<223> OTHER INFORMATION: fibrinogen binding polypeptide
<220> FEATURE:
<221> NAME/KEY: MISC_FEATURE
<222> LOCATION: (1)..(1)
<223> OTHER INFORMATION: X1 is any amino acid except Cys, Glu, Ile, Lys,
      Met or Thr
<220> FEATURE:
<221> NAME/KEY: MISC_FEATURE
<222> LOCATION: (2)..(3)
<223> OTHER INFORMATION: X2 and X3 are any amino acid except Cys
<220> FEATURE:
<221> NAME/KEY: MISC_FEATURE
<222> LOCATION: (5)..(8)
<223> OTHER INFORMATION: X5, X6, X7 and X8 are any amino acid except Cys
<220> FEATURE:
<221> NAME/KEY: MISC_FEATURE
<222> LOCATION: (10)..(11)
<223> OTHER INFORMATION: X10 and X11 are any amino acid except Cys
<220> FEATURE:
<221> NAME/KEY: MISC_FEATURE
<222> LOCATION: (12)..(12)
<223> OTHER INFORMATION: X12 is any amino acid except Cys, Glu, Ile,
      Lys, Met or Thr

<400> SEQUENCE: 27

Xaa Xaa Xaa Cys Xaa Xaa Xaa Xaa Cys Xaa Xaa Xaa
1               5                   10

<210> SEQ ID NO 28
<211> LENGTH: 13
<212> TYPE: PRT
<213> ORGANISM: artificial
<220> FEATURE:
<223> OTHER INFORMATION: 7-member cyclic peptide display template
<220> FEATURE:
<221> NAME/KEY: MISC_FEATURE
<222> LOCATION: (1)..(3)
<223> OTHER INFORMATION: X1, X2 and X3 are any amino acid except Cys
<220> FEATURE:
<221> NAME/KEY: MISC_FEATURE

```
<222> LOCATION: (5)..(9)
<223> OTHER INFORMATION: X5, X6, X7, X8 and X9 are any amino acid except
      Cys
<220> FEATURE:
<221> NAME/KEY: MISC_FEATURE
<222> LOCATION: (11)..(13)
<223> OTHER INFORMATION: X11, X12 and X13 are any amino acid except Cys

<400> SEQUENCE: 28

Xaa Xaa Xaa Cys Xaa Xaa Xaa Xaa Xaa Cys Xaa Xaa Xaa
1               5                   10

<210> SEQ ID NO 29
<211> LENGTH: 14
<212> TYPE: PRT
<213> ORGANISM: artificial
<220> FEATURE:
<223> OTHER INFORMATION: 8-member cyclic peptide display template
<220> FEATURE:
<221> NAME/KEY: MISC_FEATURE
<222> LOCATION: (1)..(3)
<223> OTHER INFORMATION: X1, X2 and X3 are any amino acid except Cys
<220> FEATURE:
<221> NAME/KEY: MISC_FEATURE
<222> LOCATION: (5)..(10)
<223> OTHER INFORMATION: X5, X6, X7, X8, X9 and X10 are any amino acid
      except Cys
<220> FEATURE:
<221> NAME/KEY: MISC_FEATURE
<222> LOCATION: (12)..(14)
<223> OTHER INFORMATION: X12, X13 and X14 are any amino acid except Cys

<400> SEQUENCE: 29

Xaa Xaa Xaa Cys Xaa Xaa Xaa Xaa Xaa Xaa Cys Xaa Xaa Xaa
1               5                   10

<210> SEQ ID NO 30
<211> LENGTH: 15
<212> TYPE: PRT
<213> ORGANISM: artificial
<220> FEATURE:
<223> OTHER INFORMATION: 9-member cyclic peptide display template
<220> FEATURE:
<221> NAME/KEY: MISC_FEATURE
<222> LOCATION: (1)..(3)
<223> OTHER INFORMATION: X1, X2 and X3 are any amino acid except Cys
<220> FEATURE:
<221> NAME/KEY: MISC_FEATURE
<222> LOCATION: (5)..(11)
<223> OTHER INFORMATION: X5, X6, X7, X8, X9, X10 and X11 are any amino
      acid except Cys
<220> FEATURE:
<221> NAME/KEY: MISC_FEATURE
<222> LOCATION: (13)..(15)
<223> OTHER INFORMATION: X13, X14, and X15 are any amino acid except Cys

<400> SEQUENCE: 30

Xaa Xaa Xaa Cys Xaa Xaa Xaa Xaa Xaa Xaa Xaa Cys Xaa Xaa Xaa
1               5                   10                  15

<210> SEQ ID NO 31
<211> LENGTH: 16
<212> TYPE: PRT
<213> ORGANISM: artificial
<220> FEATURE:
<223> OTHER INFORMATION: 10-member cyclic peptide display template
<220> FEATURE:
<221> NAME/KEY: MISC_FEATURE
<222> LOCATION: (1)..(2)
<223> OTHER INFORMATION: X1 and X2 are D, F, H, L, N, P, R, S, W, or Y
<220> FEATURE:
<221> NAME/KEY: MISC_FEATURE
<222> LOCATION: (3)..(3)
```

```
<223> OTHER INFORMATION: X3 is A, D, F, G, H, L, N, P, Q, R, S, V, W,
      or Y
<220> FEATURE:
<221> NAME/KEY: MISC_FEATURE
<222> LOCATION: (5)..(12)
<223> OTHER INFORMATION: X5, X6, X7, X8, X9, X10, X11 and X12 are any
      amino acid except Cys
<220> FEATURE:
<221> NAME/KEY: MISC_FEATURE
<222> LOCATION: (14)..(14)
<223> OTHER INFORMATION: X14 is A, D, F, G, H, L, N, P, Q, R, S, V, W,
      or Y
<220> FEATURE:
<221> NAME/KEY: MISC_FEATURE
<222> LOCATION: (15)..(16)
<223> OTHER INFORMATION: X15 and X16 are D, F, H, L, N, P, R, S, W, or Y

<400> SEQUENCE: 31

Xaa Xaa Xaa Cys Xaa Xaa Xaa Xaa Xaa Xaa Xaa Xaa Cys Xaa Xaa Xaa
1               5                   10                  15

<210> SEQ ID NO 32
<211> LENGTH: 18
<212> TYPE: PRT
<213> ORGANISM: artificial
<220> FEATURE:
<223> OTHER INFORMATION: 12-member cyclic peptide display template
<220> FEATURE:
<221> NAME/KEY: MISC_FEATURE
<222> LOCATION: (1)..(2)
<223> OTHER INFORMATION: X1 and X2 are A, D, F, G, H, L, N, P, R, S, W,
      or Y
<220> FEATURE:
<221> NAME/KEY: MISC_FEATURE
<222> LOCATION: (3)..(3)
<223> OTHER INFORMATION: X3 is any amino acid except Cys
<220> FEATURE:
<221> NAME/KEY: MISC_FEATURE
<222> LOCATION: (5)..(14)
<223> OTHER INFORMATION: X5, X6, X7, X8, X9, X10, X11, X12, X13 and X14
      are any amino acid except Cys
<220> FEATURE:
<221> NAME/KEY: MISC_FEATURE
<222> LOCATION: (16)..(16)
<223> OTHER INFORMATION: X16 is any amino acid except Cys
<220> FEATURE:
<221> NAME/KEY: MISC_FEATURE
<222> LOCATION: (17)..(18)
<223> OTHER INFORMATION: X17 and X18 are A, D, F, G, H, L, N, P, R, S,
      W, or Y

<400> SEQUENCE: 32

Xaa Xaa Xaa Cys Xaa Xaa Xaa Xaa Xaa Xaa Xaa Xaa Xaa Xaa Cys Xaa
1               5                   10                  15

Xaa Xaa

<210> SEQ ID NO 33
<211> LENGTH: 12
<212> TYPE: PRT
<213> ORGANISM: artificial
<220> FEATURE:
<223> OTHER INFORMATION: fibrinogen binding polypeptide

<400> SEQUENCE: 33

Tyr Trp Tyr Cys Asp Ser Trp His Cys Gly Val Phe
1               5                   10

<210> SEQ ID NO 34
<211> LENGTH: 12
<212> TYPE: PRT
<213> ORGANISM: artificial
<220> FEATURE:
```

```
<223> OTHER INFORMATION: fibrinogen binding polypeptide

<400> SEQUENCE: 34

His Trp Tyr Cys Thr Trp His Gly Cys Val His Trp
1               5                   10

<210> SEQ ID NO 35
<211> LENGTH: 13
<212> TYPE: PRT
<213> ORGANISM: artificial
<220> FEATURE:
<223> OTHER INFORMATION: fibrinogen binding polypeptide

<400> SEQUENCE: 35

Leu Pro Gln Cys Glu Met Tyr Gly Thr Cys Trp Thr Tyr
1               5                   10

<210> SEQ ID NO 36
<211> LENGTH: 13
<212> TYPE: PRT
<213> ORGANISM: artificial
<220> FEATURE:
<223> OTHER INFORMATION: fibrinogen binding polypeptide

<400> SEQUENCE: 36

Asp Gly Trp Cys Lys Pro Pro Leu Trp Cys Trp Gln Leu
1               5                   10

<210> SEQ ID NO 37
<211> LENGTH: 14
<212> TYPE: PRT
<213> ORGANISM: artificial
<220> FEATURE:
<223> OTHER INFORMATION: fibrinogen binding polypeptide

<400> SEQUENCE: 37

Tyr Trp Trp Cys Ala Val Trp Gly Glu Gln Cys Val Thr Arg
1               5                   10

<210> SEQ ID NO 38
<211> LENGTH: 14
<212> TYPE: PRT
<213> ORGANISM: artificial
<220> FEATURE:
<223> OTHER INFORMATION: fibrinogen binding polypeptide

<400> SEQUENCE: 38

Val Pro Ser Cys Met Val Met Asp Met Trp Cys Pro Trp Asn
1               5                   10

<210> SEQ ID NO 39
<211> LENGTH: 14
<212> TYPE: PRT
<213> ORGANISM: artificial
<220> FEATURE:
<223> OTHER INFORMATION: fibrinogen binding polypeptide

<400> SEQUENCE: 39

Trp Val Pro Cys Asp Pro Thr Trp Leu Tyr Cys Trp Ser Thr
1               5                   10

<210> SEQ ID NO 40
<211> LENGTH: 15
<212> TYPE: PRT
<213> ORGANISM: artificial
<220> FEATURE:
<223> OTHER INFORMATION: fibrinogen binding polypeptide
```

<400> SEQUENCE: 40

Trp Leu Pro Cys Ala Asp Asn Arg Trp Leu Leu Cys Phe Phe Gly
1               5                   10                  15

<210> SEQ ID NO 41
<211> LENGTH: 15
<212> TYPE: PRT
<213> ORGANISM: artificial
<220> FEATURE:
<223> OTHER INFORMATION: fibrinogen binding polypeptide

<400> SEQUENCE: 41

Pro Leu Val Cys Val Glu Ser Pro Asn Tyr His Cys Ile Val Leu
1               5                   10                  15

<210> SEQ ID NO 42
<211> LENGTH: 15
<212> TYPE: PRT
<213> ORGANISM: artificial
<220> FEATURE:
<223> OTHER INFORMATION: fibrinogen binding polypeptide

<400> SEQUENCE: 42

Pro Asn His Cys His Ala Ala Tyr Lys Pro Gly Cys Trp His Ser
1               5                   10                  15

<210> SEQ ID NO 43
<211> LENGTH: 16
<212> TYPE: PRT
<213> ORGANISM: artificial
<220> FEATURE:
<223> OTHER INFORMATION: fibrinogen binding polypeptide

<400> SEQUENCE: 43

Leu Tyr Leu Cys Asn Ser Tyr Pro Met His Pro Tyr Cys Asn Pro Ser
1               5                   10                  15

<210> SEQ ID NO 44
<211> LENGTH: 16
<212> TYPE: PRT
<213> ORGANISM: artificial
<220> FEATURE:
<223> OTHER INFORMATION: fibrinogen binding polypeptide

<400> SEQUENCE: 44

Phe Asp Tyr Cys Ser Ala Asn Thr Tyr Ser Leu Tyr Cys His Phe Phe
1               5                   10                  15

<210> SEQ ID NO 45
<211> LENGTH: 16
<212> TYPE: PRT
<213> ORGANISM: artificial
<220> FEATURE:
<223> OTHER INFORMATION: fibrinogen binding polypeptide

<400> SEQUENCE: 45

His Trp Leu Cys Met Ser Arg Trp Ile Ala Tyr Trp Cys Val Asp Asn
1               5                   10                  15

<210> SEQ ID NO 46
<211> LENGTH: 18
<212> TYPE: PRT
<213> ORGANISM: artificial
<220> FEATURE:
<223> OTHER INFORMATION: fibrinogen binding polypeptide

```
-continued

<400> SEQUENCE: 46

Gly Ser Ser Cys Ser Trp Val Lys Val Gly Trp Leu Trp Glu Cys Ala
1               5                   10                  15

Asp Asp

<210> SEQ ID NO 47
<211> LENGTH: 4
<212> TYPE: PRT
<213> ORGANISM: artificial
<220> FEATURE:
<223> OTHER INFORMATION: carboxy-terminal linker

<400> SEQUENCE: 47

Gly Gly Gly Lys
1

<210> SEQ ID NO 48
<211> LENGTH: 23
<212> TYPE: PRT
<213> ORGANISM: artificial
<220> FEATURE:
<223> OTHER INFORMATION: fibrinogen binding polypeptide

<400> SEQUENCE: 48

Ala Glu Gly Thr Gly Ser Leu Tyr Leu Cys Asn Ser Tyr Pro Met His
1               5                   10                  15

Pro Tyr Cys Asn Pro Gly Lys
            20
```

FIBRINOGEN BINDING MOIETIES

CROSS-REFERENCE TO RELATED APPLICATION

This application claims priority under 35 U.S.C. §119(e) to U.S. provisional application Ser. No. 60/367,645, filed Mar. 26, 2002.

FIELD OF THE INVENTION

The present invention relates to fibrinogen binding molecules and methods for isolating, detecting, and depleting or purifying fibrinogen from a mixture. More particularly, the invention relates to materials useful for and methods of detecting fibrinogen.

BACKGROUND OF THE INVENTION

Fibrinogen is a soluble serum protein that serves as the source of fibrin in blood to form clots that are critical to hemostasis, which is the ability of the body to control and maintain adequate blood flow after injury to the vascular system. The extensively studied human fibrinogen is a 340,000 dalton protein, which has a complex oligomeric structure that contains three pairs of related polypeptide chains, designated $(A\alpha)_2$, $(B,\beta)_2$, $\gamma_2$ polypeptide chains. Chemical structural analysis and electron microscopy have demonstrated that the protein has a trinodular structure. In particular, two $A\alpha B\beta\gamma$ subunits are oriented in an anti-parallel configuration. The amino terminal portions of the six chains are bundled together in a central "E" domain. Two coiled-coil strands extend outward from either side of the E domain to two terminal nodes, the "D" domains. These coiled-coil regions are 110 amino acids long and composed of all three chains. The D domains contain two high affinity $Ca^{2+}$ binding sites and are involved with the E domain in fibrin polymerization (see, below). Extensive disulfide bridges covalently cross-link the two subunits and stabilize the globular domains. The carboxy-terminal portions of the $A\alpha$ chains form flexible extensions beyond the D domains. The D domain contains Factor XIIIa crosslinking sites and is the primary site of plasmic digestion during fibrinolysis. Thus, the individual polypeptide chains of human fibrinogen are extensively linked by disulfide bonds to form an elongated dimeric molecule (for reviews, see, e.g., Hawiger, *Semin Hematol,* 32:99–109 (1995); Doolittle et al., *FASEB J,* 10:1464–1470 (1996)).

The biology of fibrinogen and clot (thrombus) formation has been extensively investigated in recent years, and a detailed understanding of the cascade of events leading to clot formation has emerged. There are two major activation pathways (cascades) for coagulation: the intrinsic (or contact coagulation) pathway, which requires Factors XII, IX and VIII; and the extrinsic pathway, which involves tissue factor and Factor VIII. Both pathways converge at the point of activating Factor X, the enzyme responsible for converting prothrombin to thrombin, which then cleaves fibrinogen to form fibrin monomers.

The extrinsic pathway is initiated by tissue factor, a ubiquitous cellular lipoprotein, which forms a calcium-dependent complex with Factor VII. Upon complex formation, Factor VII is activated to Factor VIIa, which converts Factor X to Factor Xa. Factor Xa converts prothrombin to thrombin in conjunction with Factor Va, calcium and phospholipid. Prothrombin conversion also occurs on endothelial surfaces and activated platelets, and requires the assembly of a complex between Factor Xa, Factor Va, and prothrombin. This conversion requires the presence of phospholipid and calcium ions.

The intrinsic or contact coagulation pathway, which is normally initiated by platelets, e.g., in a wound drawing blood. The cascade begins with the formation of a complex among Factor XII, high molecular weight kininogen, and prekallikrein. Upon complex formation, Factor XII is cleaved to Factor XIIa. After the stepwise activation of Factors XI, IX, VIII, X, and V, as in the extrinsic pathway, prothrombin is activated to thrombin. Thrombin, which is a trypsin-like serine protease, is the central regulator of hemostasis and thrombosis.

Fibrin is derived from fibrinogen, and polymerization of fibrin occurs following enzymatic cleavage of fibrinogen by thrombin. Fibrin formation from fibrinogen is a spontaneous self-assembly process resulting from the removal of fibrinopeptides by thrombin. Specifically, thrombin cleavage at the Arg16-Arg17 bond in the $A\alpha$ chains and at the Arg14-Gly15 bond on the $B\beta$ chains of fibrinogen releases fibrinopeptides A and B, and exposes the fibrin polymerization site in the E domain consisting mainly of the amino (N)-terminus of the $\alpha$ chain. This N-terminus, which bears the amino acid sequence Gly-Pro-Arg-Val (SEQ ID NO:1), binds to a complementary polymerization site on two adjacent fibrinogen chains. End-to-end association of these fibrin molecules mediated by the D domains creates a binding site for the E domain polymerization site, located on a third fibrin molecule. This DD(E) ternary complex forms a core that stabilizes the forming fibrin gel. The initial polymerization product is a linear, two-stranded protofibril. Lateral coalescence of these protofibrils results in thick fibers and a branched, three-dimensional matrix (weak clot). Lateral assembly is complex but probably involves the B polymerization site (the N-terminus of $\beta$) and trimolecular complexes formed through D domain interactions.

Adjacent fibrin monomers within the fibrils become covalently cross-linked by Factor XIIIa, a plasma transglutaminase, which is itself activated by thrombin and fibrin and which cross-links lysine 406 and glutamate 398 or glutamate 399 on opposing carboxy-terminal segments of the $\gamma$ chain (see, e.g., Chen and Doolittle, *Biochemistry,* 10:4487–4491 (1971); Purves et al., *Biochemistry,* 26: 4640–4646 (1987). Such crosslinks add mechanical stability to the fibrin network (clot) and increase resistance to clot degradation. Factor XIIIa also enhances clot stability by cross-linking specialized proteins to fibrin, including the plasmin inhibitor $\alpha_2$ antiplasmin and the adhesion protein fibronectin.

The presence of fibrinogen always provides the potential for clot formation as soon as a source of factors of either the intrinsic or extrinsic pathways is provided. Accordingly, methods to isolate, detect, or label this critical component of clot formation would be useful in a variety of fields. Conversely, the potential for clotting is particularly undesirable when blood or plasma must be stored or efficiently passed through an apparatus without clogging the apparatus or without contaminating the blood or plasma with clots, which would present a risk of occlusion leading to an ischemic event, as in stroke or myocardial farct, when the blood or plasma is subsequently returned or later administered to an individual. In such cases, a method to sequester or deplete fibrinogen from a mixture, such as blood or plasma, or from a surface, such as an apparatus or storage container, is imperative to avoid a risk of health and life.

Accordingly, needs remain for the means and methods to efficiently bind fibrinogen for a variety of purposes.

SUMMARY OF THE INVENTION

This invention provides non-naturally occurring polypeptides that bind to fibrinogen. Fibrinogen binding polypeptides may be used inter alia to bind, isolate, deplete, image, or target fibrinogen in or from a mixture or on a surface. Fibrin domain-specific fibrinogen binding polypeptides of the invention may also be used to isolate, detect, image, or target fibrin monomers or polymers that comprise a fibrin monomer released from fibrinogen. Fibrin-targeting polypeptides may be used to deliver drugs or detectable labels to a fibrin-containing site, such as a blood clot (thrombus) or an atherosclerotic plaque.

This invention provides a fibrinogen binding polypeptide comprising an amino acid sequence:

(SEQ ID NO:2)

$Xaa_1$-Trp-Tyr-Cys-$Xaa_5$-$Xaa_6$-$Xaa_7$-$Xaa_8$-Cys-$Xaa_{10}$-$Xaa_{11}$-$Xaa_{12}$ wherein:
$Xaa_1$ is His or Tyr;
$Xaa_5$ is Asp or Thr;
$Xaa_6$ is Ser or Trp;
$Xaa_7$ is His or Trp;
$Xaa_8$ is Gly or His;
$Xaa_{10}$ is Gly or Val;
$Xaa_{11}$ is His or Val; and
$Xaa_{12}$ is Phe or Trp, wherein said polypeptide binds fibrinogen.

In particular, a cyclic peptide or fibrinogen binding "loop" is disclosed comprising an amino acid sequence:

(SEQ ID NO:3)

Cys-$Xaa_2$-$Xaa_3$-$Xaa_4$-$Xaa_5$-Cys wherein:
$Xaa_2$ is Asp or Thr;
$Xaa_3$ is Ser or Trp;
$Xaa_4$ is His or Trp; and
$Xaa_5$ is Gly or His, wherein said peptide binds fibrinogen.

Preferred polypeptides according to the invention comprise an amino acid sequence selected from the group consisting of:

(SEQ ID NO:4)

Gly-Ser-Tyr-Trp-Tyr-Cys-Asp-Ser-Trp-His-Cys-Gly-Val-Phe-Ala-Pro and (SEQ ID NO:5)

Gly-Ser-His-Trp-Tyr-Cys-Thr-Trp-His-Gly-Cys-Val-His-Trp-Ala-Pro, wherein the polypeptide binds fibrinogen.

In another embodiment, this invention provides a polypeptide comprising an amino acid sequence:

(SEQ ID NO:6)

$Xaa_1$-$Xaa_2$-$Xaa_3$-Cys-$Xaa_5$-$Xaa_6$-$Xaa_7$-$Xaa_8$-$Xaa_9$-Cys-Trp-$Xaa_{12}$-$Xaa_{13}$, wherein:
$Xaa_1$ is Asp or Leu;
$Xaa_2$ is Gly or Pro;
$Xaa_3$ is Gln or Trp;
$Xaa_5$ is Glu or Lys;
$Xaa_6$ is Met or Pro;
$Xaa_7$ is Pro or Tyr;
$Xaa_8$ is Gly or Leu;
$Xaa_9$ is Thr or Trp;
$Xaa_{12}$ is Gln or Thr; and
$Xaa_{13}$ is Leu or Tyr, wherein said polypeptide binds fibrinogen.

In particular, a cyclic peptide is disclosed comprising an amino acid sequence:

(SEQ ID NO:7)

Cys-$Xaa_2$-$Xaa_3$-$Xaa_4$-$Xaa_5$-$Xaa_6$-Cys, wherein:
$Xaa_2$ is Glu or Lys;
$Xaa_3$ is Met or Pro;
$Xaa_4$ is Pro or Tyr;
$Xaa_5$ is Gly or Leu; and
$Xaa_6$ is Thr or Trp, wherein said peptide binds fibrinogen.

Preferred polypeptides according to the invention comprise an amino acid sequence selected from the group consisting of:

(SEQ ID NO:8)

Ala-Gly-Leu-Pro-Gln-Cys-Glu-Met-Tyr-Gly-Thr-Cys-Trp-Thr-Tyr-Gly-Thr and

Ala-Gly-Asp-Gly-Trp-Cys-Lys-Pro-Pro-Leu-Trp-Cys-Trp-Gln-Leu-Gly-Thr (SEQ ID NO:9), wherein the polypeptide binds fibrinogen.

In another embodiment, the present invention provides a polypeptide comprising an amino acid sequence:

(SEQ ID NO:10)

wherein:
Xaa₁ is Trp, Tyr or Val;
Xaa₂ is Pro, Trp, or Val;
Xaa₃ is Pro, Ser, or Trp;
Xaa₅ is Ala, Asp, or Met;
Xaa₆ is Pro or Val, preferably Val;
Xaa₇ is Met, Thr, or Trp;
Xaa₈ is Asp, Gly, or Trp;
Xaa₉ is Glu, Leu, or Met;
Xaa₁₀ is Gln, Trp, or Tyr;
Xaa₁₂ is Pro, Trp, or Val;
Xaa₁₃ is Ser, Thr, or Trp; and
Xaa₁₄ is Arg, Asn, or Thr, wherein said polypeptide binds fibrinogen.

In particular, a cyclic peptide is disclosed comprising an amino acid sequence:

(SEQ ID NO:11)

wherein:
Xaa₂ is Ala, Asp, or Met;
Xaa₃ is Pro or Val, preferably Val;
Xaa₄ is Met, Thr, or Trp;
Xaa₅ is Asp, Gly, or Trp;
Xaa₆ is Glu, Leu, or Met; and
Xaa₇ is Gln, Trp, or Tyr;

wherein said peptide binds fibrinogen.

Preferred polypeptides according to the invention comprise an amino acid sequence selected from the group consisting of:

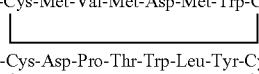
(SEQ ID NO:12)

(SEQ ID NO:13)

(SEQ ID NO:14), wherein the polypeptide binds fibrinogen.

In another embodiment, the present invention provides a polypeptide comprising an amino acid sequence:

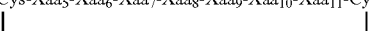
(SEQ ID NO:15)

wherein:
Xaa₁ is Pro or Trp, preferably Pro;
Xaa₂ is Asn or Leu, preferably Leu;
Xaa₃ is His, Pro, or Val;
Xaa₅ is Ala, His, or Val;
Xaa₆ is Ala, Asp, or Glu;
Xaa₇ is Ala, Asn, or Ser;
Xaa₈ is Arg, Pro, or Tyr;
Xaa₉ is Asn, Lys, or Trp;
Xaa₁₀ is Leu, Pro, or Tyr;
Xaa₁₁ is Gly, His, or Leu;
Xaa₁₃ is Ile, Phe, or Trp;
Xaa₁₄ is His, Phe, or Val; and
Xaa₁₅ is Gly, Leu, or Ser, wherein said polypeptide binds fibrinogen.

In particular, a cyclic peptide is disclosed comprising an amino acid sequence:

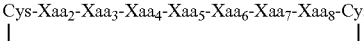
(SEQ ID NO:16)

wherein:
Xaa₂ is Ala, His, or Val;
Xaa₃ is Ala, Asp, or Glu;
Xaa₄ is Ala, Asn, or Ser;
Xaa₅ is Arg, Pro, or Tyr;
Xaa₆ is Asn, Lys, or Trp;
Xaa₇ is Leu, Pro, or Tyr; and
Xaa₈ is Gly, His, or Leu, wherein said peptide binds fibrinogen.

Preferred polypeptides according to the invention comprise an amino acid sequence selected from the group consisting of:

Ala-Gly-Trp-Leu-Pro-Cys-Ala-Asp-Asn-Arg-Trp-Leu-Leu-Cys-Phe-Phe-Gly-Gly-Thr, (SEQ ID NO:17)

Ala-Gly-Pro-Leu-Val-Cys-Val-Glu-Ser-Pro-Asn-Tyr-His-Cys-Ile-Val-Leu-Gly-Thr, and (SEQ ID NO:18)

Ala-Gly-Pro-Asn-His-Cys-His-Ala-Ala-Tyr-Lys-Pro-Gly-Cys-Trp-His-Ser-Gly-Thr, (SEQ ID NO:19)

wherein the polpeptide binds fibrinogen.

In another embodiment, the present invention provides a polypeptide comprising an amino acid sequence:

$Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-$Xaa_{12}$-Cys-$Xaa_{14}$-$Xaa_{15}$-$Xaa_{16}$, (SEQ ID NO:20)

wherein:
  $Xaa_1$ is His, Leu, or Phe;
  $Xaa_2$ is Asp, Trp, or Tyr;
  $Xaa_3$ is Leu or Tyr, preferably Leu;
  $Xaa_5$ is Asn, Met, or Ser;
  $Xaa_6$ is Ala or Ser;
  $Xaa_7$ is Arg, Asn, or Tyr;
  $Xaa_8$ is Pro, Thr, or Trp;
  $Xaa_9$ is Ile, Met, or Tyr;
  $Xaa_{10}$ is Ala, His, or Ser;
  $Xaa_{11}$ is Leu, Pro, or Tyr;
  $Xaa_{12}$ is Trp or Tyr, preferably Tyr;
  $Xaa_{14}$ is Asn, His, or Val;
  $Xaa_{15}$ is Asp, Phe, or Pro; and
  $Xaa_{16}$ is Asn, Phe, or Ser, wherein said polypeptide binds fibrinogen.

In particular, a cyclic peptide is disclosed comprising an amino acid sequence:

Cys-$Xaa_2$-$Xaa_3$-$Xaa_4$-$Xaa_5$-$Xaa_6$-$Xaa_7$-$Xaa_8$-$Xaa_9$-Cys, (SEQ ID NO:21)

wherein:

$Xaa_2$ is Asn, Met, or Ser;
  $Xaa_3$ is Ala or Ser;
  $Xaa_4$ is Arg, Asn, or Tyr;
  $Xaa_5$ is Pro, Thr, or Trp;
  $Xaa_6$ is Ile, Met, or Tyr;
  $Xaa_7$ is Ala, His, or Ser;
  $Xaa_8$ is Leu, Pro, or Tyr; and
  $Xaa_9$ is Trp or Tyr, preferably Tyr, wherein said polypeptide binds fibrinogen.

Preferred polypeptides according to the invention comprise an amino acid sequence selected from the group consisting of:

Gly-Ser-Leu-Tyr-Leu-Cys-Asn-Ser-Tyr-Pro-Met-His-Pro-Tyr-Cys-Asn-Pro-Ser-Ala-Pro, (SEQ ID NO:22)

Gly-Ser-Phe-Asp-Tyr-Cys-Ser-Ala-Asn-Thr-Tyr-Ser-Leu-Tyr-Cys-His-Phe-Phe-Ala-Pro, (SEQ ID NO:23)

-continued

Gly-Ser-His-Trp-Leu-Cys-Met-Ser-Arg-Trp-Ile-Ala-Tyr-Trp-Cys-Val-Asp-Asn-Ala-Pro, (SEQ ID NO:24)

wherein the polypeptide binds fibrinogen.

In another embodiment, the present invention provides a polypeptide comprising an amino acid sequence:

Gly-Asp-Gly-Ser-Ser-Cys-Ser-Trp-Val-Lys-Val-Gly-Trp-Leu-Trp-Glu-Cys-Ala-Asp-Asp-Pro, (SEQ ID NO:25)

wherein said polypeptide binds fibrinogen.

In particular, a stable binding loop is disclosed, having the amino acid sequence:

Cys-Ser-Trp-Val-Lys-Val-Gly-Trp-Leu-Trp-Glu-Cys, (SEQ ID NO:26)

wherein said polypeptide binds fibrinogen.

In a preferred embodiment, compositions and methods comprise a fibrinogen binding polypeptide of the invention, which specifically binds to fibrinogen at a site that will also be present on the corresponding fibrin monomer cleaved from fibrinogen during thrombosis. Such fibrin domain-specific fibrinogen binding polypeptide of the invention may be used as a fibrin-specific agent that can follow the fibrin monomer generated from fibrinogen into any site where fibrin is found, e.g., in a clot or atherosclerotic plaque. Accordingly, a fibrin domain-specific fibrinogen binding polypeptide of the invention may be detectably labeled and used to target or localize nascent fibrin rich sites in the body as they are being formed. Alternatively, a fibrin domain-specific fibrinogen binding polypeptide of the invention may be used to deliver or chaperone a drug, e.g., a thrombolytic, to sites of fibrin (e.g., clots) in the body.

Fibrinogen binding moieties of the invention may comprise a fibrinogen binding polypeptide described herein, a phage or other replicable genetic package displaying a fibrinogen binding polypeptide described herein, and molecules that comprise a fibrinogen binding polypeptide described herein further linked (covalently or non-covalently) to other molecules (such as other polypeptides, detectable molecular tags, radionuclides, drugs (such as thrombolytics), etc.).

Additional amino acids may be added to the N-terminus and/or C-terminus of any of the defined fibrinogen binding moieties of the invention, so long as the ability to bind fibrinogen is retained. Polypeptides according to the present invention will include a cyclic peptide "loop" structure as defined by one of the structures herein (see, e.g., SEQ ID NOs:2–26, supra) and will also bind to fibrinogen. Any additional amino acids included in the polypeptide must not alter the conformation so as to hinder or occlude the fibrinogen binding moiety or otherwise render the polypeptides as a whole incapable of binding fibrinogen. It will be appreciated by those skilled in the art that the presence of a defined structure according to any of the formulae disclosed herein in a larger polypeptide does not guarantee fibrinogen binding of the polypeptide as a whole, as the 3-dimensional structure of the polypeptide taken as a whole must retain a conformation permitting fibrinogen binding. Thus, a polypeptide according to the invention must both (a) comprise a structural element according to one of the formulae described herein and (b) must have the ability to bind fibrinogen.

The invention also provides methods of using a fibrinogen binding moiety to detect or isolate fibrinogen in a solution. For such methods, a fibrinogen binding moiety of the invention may be used in a variety of formats, including but not limited to, immobilized on a solid surface, such as adsorbed on the surface of a well of a multi-well assay plate, immobilized by conjugation to the surface of chromatography matrix material, such as conjugated to N-hydroxysuccinimide (NHS)-sepharose chromatography particles, or suspended or dispersed as a free, unconjugated moiety in a solution, e.g., of whole blood or a fraction thereof, which contains fibrinogen.

In a preferred embodiment, the invention provides a method of isolating fibrinogen from a solution comprising the steps of providing a fibrinogen binding moiety of the invention immobilized on a solid surface; contacting the immobilized binding moiety with the solution containing fibrinogen to permit the fibrinogen in the solution to form a binding complex with the immobilized binding moiety; separating the unbound portion of the solution from the immobilized binding moiety; and, optionally, eluting or separating the fibrinogen from the immobilized binding moiety.

The fibrinogen binding moieties of the invention may also be used to label or identify a fibrinogen molecule in a solution. In a preferred embodiment, fibrinogen is detected in a solution comprising the steps of providing a fibrinogen binding moiety, which is linked to a detectable label or tag molecule; allowing the binding moiety to form a complex with a fibrinogen molecule in the solution; and detecting the presence of the label or tag bound. Preferably, such detection assays are sensitive enough for quantitative determination of fibrinogen in a sample, i.e., where the intensity of the tag or label detected is directly proportional to the amount of fibrinogen bound in the solution.

In another method of the invention, fibrinogen binding moieties are used in blood pool imaging of an individual, such as used in diagnosing blocked blood vessels, hemorrhage of damaged blood vessels, and internal bleeding. In a preferred embodiment, the method comprises administering to an individual, a fibrinogen binding moiety linked to a detectable label. In a more preferred embodiment, the label is detectable by magnetic resonance imaging (MRI) and the label is a gadolinium (Gd)-containing label.

In yet another embodiment, the invention provides methods for increasing the serum half-life of a therapeutic or diagnostic compound of interest comprising linking the therapeutic or diagnostic compound to a fibrinogen binding moiety of the invention and administering the compound/fibrinogen binding moiety to an individual. The compound/binding moiety conjugate in the blood will associate with circulating fibrinogen molecule(s) and will remain in the serum longer than if the compound were administered in the absence of a fibrinogen binding moiety. The fibrinogen binding moiety can be selected for its particular affinity for fibrinogen, so as to tailor the behavior of the conjugate in circulation to the particular therapeutic or diagnostic need for which the conjugate is employed.

In yet another embodiment, the invention provides a method of isolating fibrinogen fusion proteins, in which a fibrinogen has been fused in frame to another polypeptide, comprising the steps of contacting a solution containing a fibrinogen fusion protein with a fibrinogen binding moiety described herein to form a complex between the fibrinogen fusion protein and the fibrinogen binding moiety; separating unbound components of the solution from the complex; and, optionally, eluting or separating the fibrinogen fusion protein from the binding moiety.

These and other aspects of the invention will be described in more detail below.

Definitions

In the following sections, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompasses DNA molecules which have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage" is defined as a bacterial virus containing a DNA core and a protective shell built up by the aggregation of a number of different protein molecules. The terms "bacteriophage" and "phage" are used herein interchangeably. Unless otherwise noted, the terms "bacteriophage" and "phage" also encompass "phagemids", i.e., bacteriophage the genome of which includes a plasmid that can be excised by coinfection of a host with a helper phage. A particular phage useful in the isolation of fibrinogen binding peptides of the invention via phage display technology is a recombinant, single-stranded DNA, filamentous M13 phage.

The term "polypeptide" refers to a polymer comprising two or more amino acid residues linked with amide bonds, and the term "peptide" is used herein to refer to relatively short polypeptides, e.g., having fewer than about 30 amino acids. The term "polypeptide" also encompasses the term "protein".

The term "binding" refers to the determination by standard techniques that a binding moiety recognizes and binds reversibly to a given target. Such standard techniques to detect or measure fibrinogen binding include ELISA, equilibrium dialysis, gel filtration, and the monitoring of spectroscopic changes that result from binding, e.g., using fluorescence anisotropy, either by direct binding measurements or competition assays with another binder.

The terms "binding moiety" as used herein refers to any molecule, peptide, or peptidomimetic capable of forming a binding complex with another molecule, peptide, peptidomimetic, or transformant. The terms "fibrinogen binding moiety", "fibrinogen binder", and "fibrinogen ligand" are terms, used herein interchangeably, that refer to any molecule, peptide, or peptidomimetic capable of forming a binding complex with fibrinogen, and those terms encompass, e.g., fibrinogen binding polypeptide, a phage displaying a fibrinogen binding polypeptide, or a transformed cell expressing a fibrinogen binding polypeptide described herein. A "fibrinogen binding moiety" also encompasses fragments of the binding polypeptides described herein which specifically bind a fibrinogen, modifications of such binding polypeptides made by incorporating the polypeptides (or fibrinogen-binding fragments thereof) in larger polypeptides while still retaining the ability to bind a fibrinogen, and derivatives of the binding polypeptides made by conservative amino acid substitutions at any position, so long as substitution does not eliminate the ability to specifically bind to a fibrinogen. Conservative substitutions for an amino acid within the sequence may be selected from other members of the class to which the amino acid belongs, i.e., nonpolar (hydrophobic) amino acids: alanine, leucine, isoleucine, valine, proline, phenylalanine, tryptophan, and methionine; polar neutral amino acids: glycine, serine, threonine, cysteine, tyrosine, asparagine, and glutamine; positively charged (basic) amino acids: arginine, lysine, and histidine; negatively charged (acidic) amino acids: aspartic acid and glutamic acid. Specific examples of fibrinogen binding moieties of the invention are the polypeptides comprising the amino acid sequences mentioned above (e.g., SEQ ID NOS:2–26), phage displaying such fibrinogen binding polypeptides, hybrid and chimeric polypeptides incorporating such polypeptides, and recombinant cells displaying any of such polypeptides. Also included within the definition of fibrin binding moieties are polypeptides which are modified as disclosed herein. Specific examples of modifications are C- or N-terminal amino acid substitutions or elongations, e.g., for the purpose of linking the binding moiety to a detectable imaging label or other substrate, examples of which include, e.g., addition of a polyhistidine "tail" in order to assist in purification; substitution of one up to several amino acids in order to obliterate an enzyme cleavage site; the use of N-terminal or C-terminal modifications or linkers, such as polyglycine or polylysine segments; alterations to include functional groups, notably hydrazide (—NH—NH$_2$) functionalities, to assist in immobilization of binding peptides according to this invention on solid supports; and the like. In addition to the detectable labels described further herein, other suitable substrates for the fibrinogen binding polypeptides include a thrombolytic agent or enzyme (e.g., tPA, plasmin, streptokinase, urokinase, hirudin), a liposome (e.g., loaded with thrombolytic agent, an ultrasound appropriate gas or both), or a solid support, well, plate, bead, tube, slide, filter, or dish. All such modified fibrinogen binding moieties are also considered fibrinogen binding moieties so long as they retain the ability to bind fibrinogen.

A "fibrinogen-like" polypeptide is any compound comprising two or more consectuive amino acid residues found in fibrinogen comprising a site on the fibrinogen protein that is bound by a fibrinogen binding moiety of the invention. Accordingly, "fibrinogen-like polypeptide" is a broad term that includes any fibrinogen, fragment thereof, mutant form thereof, and any other polypeptide, whether recombinant, non-naturally occurring, or naturally occurring, that is bound by a fibrinogen binding moiety of the invention.

The terms "DD", "DD dimer", and "DD(E)" refer to fibrin subcomponents typically generated by proteolytic degradation of fibrin with plasmin or trypsin. The terms "DD" and "DD dimer" both refer to the glutaminase crosslinked D domains of adjacent fibrin monomers, about 180 kDa in molecular weight. The term "DD dimer" encompasses the C-terminal portion of fibrin, including roughly α(111–197), β(134–461) and γ(88–406) in the human fibrinogen sequence. The term "DD(E)" refers to a complex of DD with the central E domain of fibrin, about 60 kDa in molecular weight, and roughly includes α(111–197), β(134–461), γ(88–406), α(17–78), β(15–122) and γ(1–62) in the human fibrinogen sequence. Since "DD" and "DD(E)" are products of proteolysis of fibrin, there may be some slight heterogeneity in their composition, depending on the mode of protease digestion and their subsequent isolation. (See, Olexa et al., *Biochemistry*, 20: 6139–6145 (1981); Moskowitz and Budzynski, *Biochemistry*, 33: 12937–12944 (1994); Spraggon et al., *Nature*, 389: 455–462 (1997); and references therein.)

The term "specificity" refers to a binding moiety having a higher binding affinity for one target over another. The term "fibrinogen specificity" refers to a fibrinogen binding moiety having a higher affinity for fibrinogen over an irrelevant target, e.g., serum albumin. Binding specificity may be characterized by a dissociation equilibrium constant ($K_D$) or an association equilibrium constant ($K_a$) for the two tested target materials. The binding polypeptides according to the present invention are specific for fibrinogen and preferably have a $K_D$ for fibrinogen that is lower than 50 µM, more preferably less than 10 µM, most preferably less than 1 µM or even lower.

The term "metal chelate" as used herein refers to a physiologically compatible compound consisting of one or more cyclic or acyclic multidentate organic ligands complexed to one or more paramagnetic metal ions with atomic numbers 21–29, 42, 44, or 57–83.

The term "capable of complexing a paramagnetic metal" as used herein refers to the chemical groups on a chelator which have the ability to complex a paramagnetic metal by non-covalent forces. As used herein, the phrase "the chelator complexes the metal" means an aggregate of the chelator and metal ion held together by non-covalent forces. The term "coupled" as used herein broadly includes any attachment of the chelator to the peptide.

DETAILED DESCRIPTION OF THE INVENTION

Figure 1:
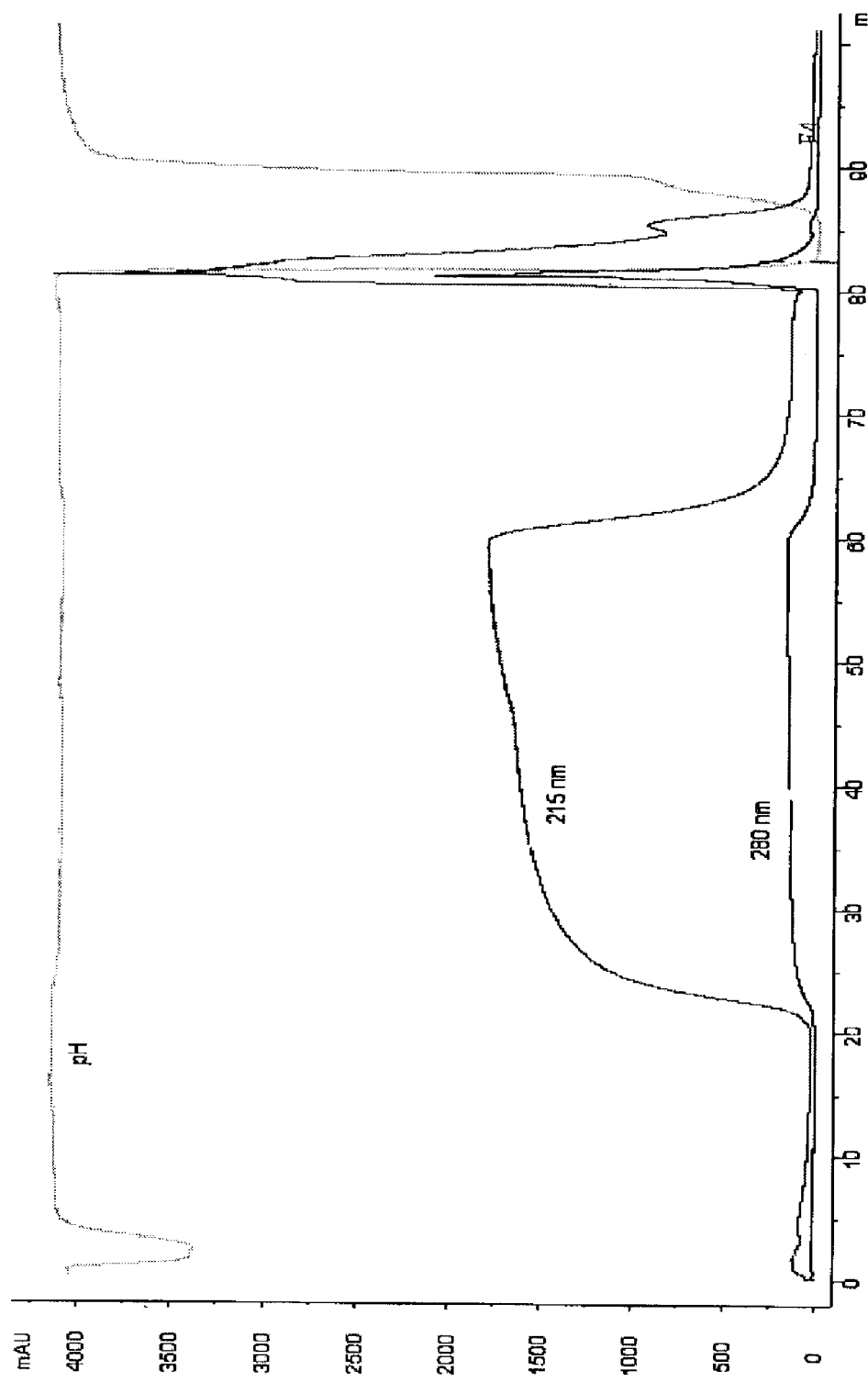
FIG. 1 is a chromatogram illustrating the purified fibrinogen binding capacity of a fibrinogen binding column utilizing the fibrinogen binding peptide of SEQ ID NO:48 and having a ligand density of 2.0 µM/ml resin. Purified fibrinogen (0.5 mg/ml in PBS) was injected continuously onto the column until the A280 reading reached a plateau. The column was then washed with PBS until a baseline reading was obtained and then eluted with glycine buffer (0.1M, pH 2.5). The eluted fraction (major peak) was collected and analyzed by HPLC Size Exclusion Chromatography (SEC). The capacity of the column was calculated to be 2.076 mg fibrinogen/ml resin.

The present invention provides novel, non-naturally occurring binding moieties that bind fibrinogen. The fibrinogen binding moieties were unexpectedly isolated from a population of molecules that had been screened in a procedure designed to isolate moieties that specifically bind fibrin.

The fibrinogen binding moieties of the invention may be used in any of a variety of preparative and diagnostic protocols in which it is desirable to sequester, deplete, or detect fibrinogen. The preferred binding moieties of the present invention bind fibrinogen and/or fibrinogen-derived polypeptides with high affinity, i.e., acting at low, physiologically relevant concentrations, comparable to known anti-fibrinogen antibodies and other fibrinogen-binding proteins. The fibrinogen binding moieties described herein may be used in a variety of preparative or diagnostic methods, including, but not limited, depleting fibrinogen from various mixtures, including blood and blood subfractions (e.g., plasma), purifying fibrinogen from a solution, detecting fibrinogen in a mixture, localizing fibrinogen, and labeling fibrinogen with a detectable marker. Depleting samples of blood or sub-fractions of blood, such as plasma, of fibrinogen is particularly useful to prevent undesired clotting, for example, during storage or administration to a patient.

Specific fibrinogen binding polypeptides according to the present invention were isolated initially by screening of phage display libraries, that is, populations of recombinant bacteriophage transformed to express an exogenous peptide loop on their surface. In order to isolate new polypeptide binding moieties for a particular target, such as fibrinogen, screening of large peptide libraries, for example using phage display techniques, is especially advantageous, in that very large numbers (e.g., $5 \times 10^9$) of potential binders can be tested and successful binders isolated in a short period of time.

In order to prepare a phage library of potential polypeptides to screen for binding moieties such as fibrin binding peptides, a candidate binding domain is selected to serve as a structural template for the peptides to be displayed in the library. The phage library is made up of a multiplicity of analogues of the parental domain or template. It is not essential that the domain selected to act as a template for the library have any affinity for the target at all, its purpose is to provide a structure from which a multiplicity (library) of similarly structured polypeptides (analogues) can be generated, which multiplicity of analogues will hopefully include one or more analogues that exhibit the desired binding properties (and any other properties selected for).

In selecting the parental binding domain or template on which to base the variegated amino acid sequences of the library, an important consideration is how the variegated peptide domains will be presented to the target, i.e., in what conformation the peptide analogues will come into contact with the target. In phage display methodologies, for example, the analogues (display peptides) will be generated by insertion of synthetic DNA encoding the analogues into the coding region of a phage surface protein gene, resulting in display of the analogue on the surfaces of the phage. Such libraries of phage, such as M13 phage, displaying a wide variety of different polypeptides, can be prepared using techniques as described, e.g., in Kay et al., *Phage Display of Peptides and Proteins: A Laboratory Manual* (Academic Press, Inc., San Diego 1996) and U.S. Pat. No. 5,223,409 (Ladner et al.), incorporated herein by reference.

In isolating the specific polypeptides according to this invention, a series of M13 phage display libraries were screened, initially to isolate fibrin binders. The fibrinogen binders disclosed herein were discovered among the fibrin binders. The libraries all employed a template encoding a cyclic polypeptide display of 6–12 amino acids. The libraries are designated TN6/VI (having a potential $3.3 \times 10^{12}$ amino acid sequence diversity), TN7/IV (having a potential $1.2 \times 10^{14}$ amino acid sequence diversity), TN8/IX (having a potential $2.2 \times 10^{15}$ amino acid sequence diversity), TN9/IV (having a potential $4.2 \times 10^{16}$ amino acid sequence diversity, TN10/IX (having a potential $3.0 \times 10^{16}$ amino acid sequence diversity), TN12/I (having a potential amino acid sequence diversity of $4.6 \times 10^{19}$).

The TN6/VI library was constructed to display a single microprotein binding loop contained in a 12-amino acid template. The TN6/VI library utilized a template sequence of (SEQ ID NO:27)

$Xaa_1\text{-}Xaa_2\text{-}Xaa_3\text{-}Cys\text{-}Xaa_5\text{-}Xaa_6\text{-}Xaa_7\text{-}Xaa_8\text{-}Cys\text{-}Xaa_{10}\text{-}Xaa_{11}\text{-}Xaa_{12}$.

The amino acids at positions 2, 3, 5, 6, 7, 8, 10, and 11 of the template were varied to permit any amino acid except cysteine (Cys). The amino acids at positions 1 and 12 of the template were varied to permit any amino acid except cysteine (Cys), glutamic acid (Glu), isoleucine (Ile), Lysine (Lys), methionine (Met), and threonine (Thr).

The TN7/IV library was constructed to display a single microprotein binding loop contained in a 13-amino acid template. The TN7/IV library utilized a template sequence of (SEQ ID NO:28)

$Xaa_1\text{-}Xaa_2\text{-}Xaa_3\text{-}Cys\text{-}Xaa_5\text{-}Xaa_6\text{-}Xaa_7\text{-}Xaa_8\text{-}Xaa_9\text{-}Cys\text{-}Xaa_{11}\text{-}Xaa_{12}\text{-}Xaa_{13}$.

The amino acids at amino acid positions 1, 2, 3, 5, 6, 7, 8, 9, 11, 12, and 13 of the template were varied to permit any amino acid except cysteine (Cys).

The TN8/IX library was constructed to display a single microprotein binding loop contained in a 14-amino acid template. The TN8/IX library utilized a template sequence of (SEQ ID NO:29)

$Xaa_1\text{-}Xaa_2\text{-}Xaa_3\text{-}Cys\text{-}Xaa_5\text{-}Xaa_6\text{-}Xaa_7\text{-}Xaa_8\text{-}Xaa_9\text{-}Xaa_{10}\text{-}Cys\text{-}Xaa_{12}\text{-}Xaa_{14}$.

The amino acids at position 1, 2, 3, 5, 6, 7, 8, 9, 10, 12, 13, and 14 in the template were varied to permit any amino acid except cysteine (Cys).

The TN9/IV library was constructed to display a single microprotein binding loop contained in a 15-amino acid template. The TN9/IV library utilized a template sequence (SEQ ID NO:30)

$Xaa_1\text{-}Xaa_2\text{-}Xaa_3\text{-}Cys\text{-}Xaa_5\text{-}Xaa_6\text{-}Xaa_7\text{-}Xaa_8\text{-}Xaa_9\text{-}Xaa_{10}\text{-}Xaa_{11}\text{-}Cys\text{-}Xaa_{13}\text{-}Xaa_{14}\text{-}Xaa_{15}$.

The amino acids at position 1, 2, 3, 5, 6, 7, 8, 9, 10, 11, 13, 14 and 15 in the template were varied to permit any amino acid except cysteine (Cys).

The TN10/IX library was constructed to display a single microprotein binding loop contained in a 16-amino acid template. The TN10/IX library utilized a template sequence of (SEQ ID NO:31)

$Xaa_1\text{-}Xaa_2\text{-}Xaa_3\text{-}Cys\text{-}Xaa_5\text{-}Xaa_6\text{-}Xaa_7\text{-}Xaa_8\text{-}Xaa_9\text{-}Xaa_{10}\text{-}Xaa_{11}\text{-}Xaa_{12}\text{-}Cys\text{-}Xaa_{14}\text{-}Xaa_{15}\text{-}Xaa_{16}$.

The amino acids at positions 1, 2, 15, and 16 in the template were varied to permit any amino acid selected from a group of 10 amino acids: D, F, H, L, N, P, R, S, W, or Y). The amino acids at positions 3 and 14 in the template were varied to permit any amino acid selected from a group of 14 amino acids: A, D, F, G, H, L, N, P, Q, R, S, V, W, or Y). The amino acids at positions 5, 6, 7, 8, 9, 10, 11, and 12 in the template were varied to permit any amino acid except cysteine (Cys).

The TN12/I library was constructed to display a single microprotein binding loop contained in an 18-amino acid template. The TN12/I library utilized a template sequence $Xaa_1$-$Xaa_2$-$Xaa_3$-Cys-$Xaa_5$-$Xaa_6$-$Xaa_7$-$Xaa_8$-$Xaa_9$-$Xaa_{10}$-$Xaa_{11}$-$Xaa_{12}$-$Xaa_{13}$-$Xaa_{14}$-Cys-$Xaa_{16}$-$Xaa_{17}$-$Xaa_{18}$.  (SEQ ID NO:32)

The amino acids at position 1, 2, 17, and 18 in the template were varied to permit any amino acid selected from a group of 12 amino acids: A, D, F, G, H, L, N, P, R, S, W, or Y). The amino acids at positions 3, 5, 6, 7, 8, 9, 10, 11, 12, 13, 14, and 16 were varied to permit any amino acid except cysteine (Cys).

Each of the cyclic peptide display libraries was created by making a designed series of mutations or variations within a coding sequence for the polypeptide template, each mutant sequence encoding a binding loop analogue corresponding in overall structure to the template except having one or more amino acid variations in the sequence of the template. The novel variegated (mutated) DNA provides sequence diversity, and each transformant phage displays one variant of the initial template amino acid sequence encoded by the DNA, leading to a phage population (library) displaying a vast number of different but structurally related amino acid sequences. The amino acid variations are expected to alter the binding properties of the binding loop or domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). As indicated previously, the techniques discussed in Kay et al., *Phage Display of Peptides and Proteins: A Laboratory Manual* (Academic Press, Inc., San Diego 1996) and U.S. Pat. No. 5,223,409 are particularly useful in preparing a library of potential binders corresponding to the selected parental template.

In a typical screen, a phage library is contacted with and allowed to bind the target, in this case, fibrin or a particular subcomponent, such as DD(E), presenting structures unique to the polymerized form of fibrin found in clots. To facilitate separation of binders and non-binders, it is convenient to immobilize the target on a solid support. Since fibrin is already insoluble, it is readily adaptable to phage screening. Soluble targets such as DD(E), on the other hand, must be immobilized by chemical modification. Phage bearing a target-binding moiety form a complex with the target on the solid support whereas non-binding phage remain in solution and may be washed away with excess buffer. Bound phage are then liberated from the target by changing the buffer to an extreme pH (pH 2 or pH 10), changing the ionic strength of the buffer, adding denaturants, or other known means. The recovered phage may then be amplified through infection of bacterial cells and the screening process repeated with the new pool that is now depleted in non-binders and enriched in binders. Alternatively, the binding phage need not even be removed from the support, but can be used to directly infect bacteria. The recovery of even a few binding phage is sufficient to carry the process to completion.

After a few rounds of selection, the gene sequences encoding the binding moieties derived from selected phage clones in the binding pool are determined by conventional methods, described below, revealing the peptide sequence that imparts binding affinity of the phage to the target. When the selection process works, the sequence diversity of the population falls with each round of selection until only good binders remain. The sequences converge on a small number of related binders, typically 10–50 out of the more than 10 million original candidates. An increase in the number of phage recovered at each round of selection, and of course, the recovery of closely related sequences are good indications that convergence of the library has occurred in a screen. After a set of binding polypeptides is identified, the sequence information may be used to design other secondary phage libraries, biased for members having additional desired properties.

Polypeptides according to the invention may be prepared in a variety of ways:

Direct synthesis of the polypeptides of the invention may be accomplished using conventional techniques, including solid-phase peptide synthesis, solution-phase synthesis, etc. Solid-phase synthesis is preferred. See, Stewart et al., *Solid-Phase Peptide Synthesis* (1989), W. H. Freeman Co., San Francisco; Merrifield, *J. Am. Chem. Soc.*, 85:2149–2154 (1963); Bodanszky and Bodanszky, *The Practice of Peptide Synthesis* (Springer-Verlag, New York 1984), incorporated herein by reference. Polypeptides according to the invention may also be prepared commercially by companies providing peptide synthesis as a service (e.g., BACHEM Bioscience, Inc., King of Prussia, Pa.; Quality Controlled Biochemicals, Inc., Hopkinton, Mass.). Automated peptide synthesis machines, such as those manufactured by Perkin-Elmer Applied Biosystems, also are available.

For producing binding polypeptides using recombinant DNA methods, a variety of expression vector systems are currently available which permit the insertion and expression of a polynucleotide sequence encoding a polypeptide. Such vectors include, for example, eukaryotic and prokaryotic expression plasmids, recombinant bacteriophage, recombinant eukaryotic viral vectors, artificial chromosomes, and the like, which also contain the transcription and translation control signals necessary for expression of the polypeptide in an appropriate host cell. In this approach, a polynucleotide sequence encoding a fibrinogen binding peptide of the invention is synthesized, e.g., using an automated DNA synthesizer, and inserted using standard methods into a selected expression vector. The resulting recombinant expression vector containing the inserted polynucleotide is then inserted into an appropriate host cell, e.g., using transformation, electroporation, microprojectiles, liposome-mediated transformation, transfection, and the like. Host cells containing the recombinant expression vector are then incubated in appropriate conditions to permit expression of the fibrinogen binding peptide, which may then be purified away from host cell proteins.

Although recombinant DNA methods are well developed for expressing heterologous polypeptides and proteins, the relatively small size of the fibrinogen binding polypeptides described herein favors the use of automated peptide synthesis as the more preferred method of producing the peptides. In addition, in vitro peptide synthesis methods permit modifications to be made on the binding peptide, such as the addition of an amino and/or a carboxy terminal capping group, which can protect the binding peptide from degradation or undesired reaction with other molecules, and/or which can provide additional groups that add to the versatility of the peptides, such as incorporating a functional group that permits coupling to an activated affinity resin, such as activated N-hydroxysuccinimide (NHS)-sepharose affinity chromatography resin particles. Binding peptides produced by standard automated peptide synthesis procedures can be easily purified, e.g., using standard reverse phase high performance liquid chromatography (HPLC), in useful amounts.

The binding properties of a fibrinogen binding moiety of the invention, either as purified binding peptides or phage displaying binding peptides, can be readily assessed using various assay formats known in the art. Such methods include fluorescence anisotropy, which provides a convenient and accurate method of determining a dissociation constant ($K_D$) of a binding moiety for a fibrinogen from one or more different species. In one such procedure, a binding moiety described herein is labeled with fluorescein. The fluorescein-labeled binding moiety may then be mixed in wells of a multi-well assay plate with various concentrations of a particular species of fibrinogen. Fluorescence anisotropy measurements are then carried out using a fluorescence polarization plate reader.

Another format to detect or measure binding to a fibrinogen in a solution uses a setup based on standard enzyme linked immunosorbent assays (ELISAs) in which a fibrinogen target is immobilized on the surface of the wells of a multi-well assay plate, and a solution comprising a fibrinogen binding moiety (polypeptide or phage) is added to the wells. The binding moiety will, under appropriate conditions, bind to the immobilized fibrinogen target, and unbound components of the solution may then be removed from the well. The presence of any binding moiety retained in the wells can then be detected with a labeled antibody (or other labeled molecule) that will bind to the binding moiety. The label on the antibody is preferably an enzyme, such as HRP, which is capable of generating a detectable signal in the presence of an appropriate substrate (TMB in the case of HRP). The intensity of the signal is proportional to the amount of binding moiety bound to the fibrinogen.

A fibrinogen binding moiety described herein may be linked (covalently or non-covalently) to various molecules and particles, including but not limited to the surface of finely divided chromatography resin particles, the surface of magnetic particles or microspheres, radionuclides, magnetic resonance imaging compounds, other polypeptides, enzymes, proteins present on of the surface cells, streptavidin, biotin, antibodies, and therapeutic compounds. A variety of methods for linking two molecules together are known in the art. Such linkages are preferably covalent linkages, although in some arrangements, a fibrinogen binding moiety of the invention may be linked to another molecule by hydrophobic or ionic linkages, or even some combination of various types of bonds. Covalent linkages useful in linking a fibrinogen binding moiety described herein to another molecule include, but are not limited to, peptide linkages, disulfide linkages, ester linkages, and ether linkages. For example, an amino group of the side chain of a lysine residue present in a fibrinogen binding moiety of the invention may be used to covalently link the binding moiety to another protein, surface, or particle via condensation to form a peptide bond. If a fibrinogen binding polypeptide of the invention is to be linked to another polypeptide of known amino acid sequence, then a fusion polypeptide comprising the two constituent molecules may be synthesized directly using an automated peptide synthesizer or using any of the various standard recombinant DNA methods known in the art for producing fusion proteins.

Covalent linking of a fibrinogen binding polypeptide or moiety of the invention to another molecule may also be achieved using any of a variety of coupling agents and protocols known in the art. Such coupling agents include, but are not limited to, non-specific coupling agents, such as glutaraldehyde; heterobifunctional coupling agents, which can link two different molecules using a different chemical reaction for each component molecule; and homobifunctional coupling agents, which can link two different molecules using the same chemical reaction for each component molecule.

Fibrinogen binding moieties of the invention may also be immobilized to the surface of a solid support material. Such solid support materials include, but are not limited to, paper, glass, plastic, wood, nylon, rubber, metal, acrylamide, cellulose, agarose, and combinations thereof. Such solid surfaces may be found in a variety of compositions, including but not limited to, wells of a multi-well assay plate, magnetic particles or beads, chromatographic resin particles, and various tubes and containers for assays and storage. A fibrinogen binding moiety may be linked to such surfaces by any of the possible types of known chemical bonds, such as covalent linkage, hydrophobic interaction, ionic linkage, and combinations thereof. For example, in some cases, a fibrinogen binding polypeptide or moiety may simply adhere to a solid surface, such as the surface of wells of a multi-well assay plate. Alternatively, a fibrinogen binding moiety may be immobilized to a solid surface using a linker molecule that tethers the binding moiety from the surface of the solid support material. In still another arrangement, the streptavidin-biotin partners may be employed to immobilize a binding moiety to the surface of solid support material.

When immobilized on solid supports such as magnetic beads, filters, or chromatography media, the binding moieties of the present invention provide useful separation media for the recovery of fibrinogen or fibrinogen-like polypeptides, including fibrinogen fusion proteins, from solutions including whole blood, blood fractions, and conditioned media containing recombinant fibrinogen or fibrinogen-like polypeptides. Once bound, the fibrinogen or fibrinogen-like polypeptides may be eluted using an appropriate elution buffer. Selecting an appropriate elution buffer is within the skill of the art and will vary depending on the desired elution conditions. Preferred eluants for use with the fibrinogen binders of the present invention include citrate buffers, e.g., 0.1M citrate pH 3.0, and, particularly preferred, glycine buffers, e.g., 100 mM glycine pH2.5.

Whatever means is used to link a binding moiety described herein to another molecule, the desired final product is preferably a compound in which there has been no significant loss of the desired characteristics of each of the component molecules: in the case of the fibrinogen binding moiety component, there is preferably no significant reduction in the ability to bind fibrinogen. More preferably, linkage of a binding moiety described herein with another molecule results in enhanced properties, such as enhanced detectability, increased serum half-life, enhanced solubility, or enhanced therapeutic efficacy.

Uses for Fibrinogen Binding Moieties of the Invention

For detection of fibrinogen in a solution, such as blood or conditioned media suspected of containing it, a fibrinogen binding moiety described herein may be detectably labeled (e.g., radiolabeled or enzymatically labeled) using standard methods, then contacted with the solution in which the binding moiety binds and forms a complex with the fibrinogen. Thereafter, formation of the binding moiety/fibrinogen complex may be detected by any of a variety of standard methods. For example, a recombinant phage displaying a fibrinogen binding polypeptide on its surface, may form a complex with fibrinogen that is detectable as a sediment in a reaction tube, which may be detected visually after settling or centrifugation. As another example, a sandwich-type assay may be used in which a fibrinogen binding moiety described herein is immobilized on a solid support such as the wall of a plastic tube, the surface of a well in a multi-well assay plate, or a chromatographic matrix particle. A solution suspected of containing fibrinogen is then contacted with the immobilized binding moiety, and non-binding components of the solution are removed or washed away. Any fibrinogen bound to the immobilized binding moiety is detected using a suitable detection reagent, such as a monoclonal antibody recognizing the fibrinogen target, which reagent is detectable by some conventional means known in the art, such as a radiolabel or conjugated enzyme that produces a detectable signal.

The fibrinogen binding moieties according to this invention are also useful for isolating fibrinogen from a solution by affinity chromatography. For example, a fibrinogen binding moiety of the invention may be linked by methods available in the art to the surface of a finely divided chromatography matrix resin, such as N-hydroxysuccinimide (NHS)-sepharose affinity resin particles, to make a fibrinogen-specific affinity chromatography resin. The immobilized binding moiety can then be loaded or contacted with a feed stream under conditions favorable to formation of binding moiety/fibrinogen complexes. Non-binding components can be removed or washed away, then the fibrinogen can be eluted by introducing solution conditions favoring dissociation of the binding complex.

Alternatively, fibrinogen may be isolated or detected by combining a solution containing the fibrinogen with a fibrinogen binding moiety described herein, then isolating complexes of the fibrinogen and the fibrinogen binding moiety. For this type of separation, many methods are known for which a fibrinogen binding moiety may be employed as the binding reagent. For example, a fibrinogen binding moiety of the invention can be immobilized on a solid support, then separated from the feed stream along with any fibrinogen bound to the binding moiety by filtration. Alternatively, a binding moiety described herein may be modified with its own affinity tag, such as a polyHis tail, which can be used to capture (bind) the binding moiety after complexes have formed using metal affinity chromatography. Once separated, the fibrinogen target can be released from the binding molecule under suitable elution conditions and recovered in pure form. Any other affinity tag and its binding partner (e.g., biotin/streptavidin, Fc/protein A, and the like) may be used in this way to make a fibrinogen binding moiety according to the invention capable of being captured or immobilized as described above.

Methods of detecting and isolating fibrinogen, as described herein, may also be used to detect and isolate fibrinogen-like polypeptides, especially fibrinogen fusion proteins comprising a mammalian fibrinogen or portion thereof linked to another polypeptide.

Since fibrinogen is an abundant protein in blood, fibrinogen binding moieties described herein may be used as reagents to localize and image blood in an individual. Such "blood pool imaging" methods typically will use magnetic resonance imaging (MRI) to obtain images of the blood in various tissues, e.g., to detect circulation or lack of it in blood vessels or to detect reperfusion of organs to which blood flow was previously blocked. See, e.g., WO 97/30734. According to the invention, a fibrinogen binding moiety is linked by standard methods to a detectable label. The labeled binding moiety is then administered to an individual, who is scanned with the appropriate detection apparatus to obtain an image of the blood in the tissue. Such blood pool imaging is particularly useful in imaging circulating blood, blockages in circulatory blood (ischemia), and in locating sites of internal bleeding in the tissues of an individual.

It is understood that using the detection or isolation methods described herein, fibrinogen (or fibrinogen-like protein) may be detected in or isolated from any of a variety of solutions that may contain fibrinogen. Such solutions include, but are not limited to, blood and blood fractions, extracts of eukaryotic cells that express fibrinogen, extracts of recombinant prokaryotic cells that express fibrinogen, and various solutions or cell extracts from transgenic animals that have been genetically engineered to express fibrinogen.

Another use for the binding moieties of the invention is to increase the half-life and overall stability of a therapeutic or diagnostic compound that is administered to or enters the circulatory system of an individual. See, e.g., U.S. Pat. No. 5,116,944; EP-A2-395 918; WO 91/01743. In such methods, a fibrinogen binding moiety described herein is used to link a therapeutic or diagnostic compound to fibrinogen found in the blood of an individual who will receive the therapeutic or diagnostic compound. In this embodiment, a fibrinogen binding moiety of the invention is linked, covalently or non-covalently, to a selected therapeutic or diagnostic compound at a site that keeps the fibrinogen binding site of the moiety intact and still capable of binding to fibrinogen, without compromising the desired diagnostic or therapeutic activity. In this way, the binding moiety serves as a linker molecule to link the diagnostic/therapeutic compound of interest to fibrinogen circulating in the blood. Linking a diagnostic or therapeutic compound to circulating fibrinogen using a fibrinogen binding moiety of the invention is expected to be particularly useful in increasing the circulating half-life and/or overall stability of compounds that are normally subject to an undesirably rapid rate of degradation or clearance from circulation. Increasing the half-life or overall stability of a compound in the circulatory system is likely to reduce the number and/or size of doses that must be administered to an individual to obtain a desired effect. Any suitable diagnostic compound may be linked to fibrinogen in this manner, including, especially detectable labels, which may be dyes (such as fluorescein); radiolabels such as $^{131}I$ or a technetium ($Tc^{99}$)-containing compound; enzymes (such as horseradish peroxidase); or a detectable metal (such as a paramagnetic ion). Any suitable therapeutic compound may be linked to fibrinogen in this manner, including drugs, biopharmaceuticals, and any polypeptide of interest. Examples of such therapeutics suitable for linking to fibrinogen include but are not limited to receptor agonists or antagonists, specific binding compounds, enzyme inhibitors, metal chelators, molecular scavengers such as vitamin E, and the like. Of particular interest for this use are thrombin inhibitors, thrombolytics (such as tPA and urokinase), renin inhibitors, ACE inhibitors, selectin ligands, inhibitors of the coagulation cascade, complement regulatory molecules (such as DAF, CR1, CR2, C4bp, factor H), serine proteases, GPIIb/IIIa antagonists, CRF antagonists, and the like.

In a particularly preferred embodiment, a fibrin domain-specific fibrinogen-binding polypeptide is linked, either covalently or non-covalently, with a pharmaceutically effective drug (including prodrugs), which has an activity that is desired only or preferentially at a site of clot formation. The resulting fibrinogen binding moiety containing the attached drug may thus be used to deliver the drug or prodrug to the site of clot formation when the fibrin monomer is cleaved from the fibrinogen and incorporated into the developing clot. In a particularly preferred embodiment, the drug is a thrombolytic to dissolve and inhibit clot formation, thereby providing an effective treatment for thrombus associated diseases.

Isolation and characterization of fibrinogen binding moieties in accordance with this invention will be further illustrated below. The specific parameters included in the following examples are intended to illustrate the practice of the invention, and they are not presented to in any way limit the scope of the invention.

EXAMPLES

Example 1

Preparation of a Fibrin Target for Library Screening

Fibrinogen binding polypeptides disclosed herein were isolated in a procedure to obtain fibrin-binding polypeptides from a series of phage display libraries exhibiting variegated short cyclic display peptides.

For screening libraries to isolate binding moieties for fibrin, two fibrin targets, i.e., synthetic fibrin clots and then a soluble fibrin fragment, DD(E), were prepared. To prepare fibrin for screening, dilute fibrin clots were formed in the wells of a 96-well plate, dried down to a thin layer, and then rehydrated prior to library screening. In a typical procedure, a 0.15 mg/ml fibrinogen solution was prepared in TBS buffer (50 mM Tris, 150 mM NaCl, pH 7.4). A solution containing 2 U/ml thrombin, 10 mM $CaCl_2$, and 5 mM ε-aminocaproic acid in TBS was prepared. The fibrinogen solution and thrombin solution were mixed 1:1 in the wells of a 96-well plate, aliquoting 25 μL of each solution in each well (total volume=50 μL). The plates were evaporated to dryness by incubating them at 37° C. overnight. Just before a phage library was added to the dried fibrin target, the fibrin wells were washed three times for 10 minutes with phage blocking buffer (TBS containing 2 mM $CaCl_2$, 0.1% Tween-20, and 0.1% human serum albumin (HSA)).

The soluble fibrin-derived polypeptide DD(E) was prepared following a modification of a published method (Moskoitz and Budzynksi, *Biochemistry*, 33: 12937–12944 (1994) and references therein). Fibrinogen containing a Factor XIII trace impurity (1 g, Grade L; purchased from American Diagnostica) was dissolved in TBS buffer and dialyzed overnight against TBS containing 5 mM citrate. The fibrinogen concentration was adjusted to 3.0 mg/ml and $CaCl_2$ was added to a concentration of 10 mM. Clotting of the fibrinogen was initiated by the addition of thrombin to 0.5 U/ml and the clot was incubated for 3 hours at 37° C. The clot was cut up with a spatula to release water and to concentrate the clot. The clot pieces were washed twice with TBS·Ca buffer (TBS containing 2 mM $CaCl_2$) and were centrifuged at 4,000×g to compact the clots between washes. The clot material was resuspended in 250 ml TBS containing 25 mM $CaCl_2$ and 2 K.I.U. plasmin per mg fibrin. The clots were digested overnight at 20° C. Undigested clot was removed by pipette, and the supernatant was shaken with 10 ml of Lysine Sepharose (Pharmacia) for 30 minutes and filtered to remove the resin. Aprotinin was added to the filtrate to a concentration of 500 U/μL. Ammonium Sulfate was added to 30% saturation and the precipitated protein was removed by centrifugation. More ammonium sulfate was added to the supernatant to a final concentration of 50% saturation, and the precipitated protein was concentrated by centrifugation. The pellets, containing DD(E), were resuspended in a small volume of buffer (50 mM Tris, 150 mM NaCl, 2 mM $CaCl_2$) (<10 ml) and chromatographed on a Sephacryl S200 (Pharmacia) size exclusion column (5×100 cm) in the same buffer. Fractions of protein eluted from the column were assayed by SDS-PAGE for DD(E). DD(E) contains subunits of 55 kD (Fragment E) and 190 kD (Fragment DD).

To prepare the DD(E) as a target for library screening, the complex was first biotinylated. The buffer was changed to 50 mM sodium phosphate and reacted with 10 equivalents of sulfo-NHS-biotin (Pierce Chemical Co.), an amino-functional compound that adds biotin moiety to amine-reactive sites. The biotin binding protein streptavidin was then immobilized by passive binding to the bottom of the wells of polystyrene 96-well microtiter plates, and the biotinylated DD(E) was added to these plates. Roughly 100 pmol of DD(E) were immobilized per well. Excess DD(E) was washed off the plates, which were then incubated with buffer containing 50 mM Tris, 150 mM NaCl, 2 mM $CaCl_2$, 0.05% Tween-20, and 0.1% human serum albumin to block sites against nonspecific binding.

Example 2

Screening of Phage Display Libraries

The following phage libraries screened in this protocol yielded representative fibrinogen binding polypeptides of this invention: TN6/VI library ($3.3 \times 10^{12}$ amino acid diversity), TN7/IV ($5 \times 10^9$ amino acid sequence diversity), TN8/IX ($6 \times 10^9$ amino acid sequence diversity), TN9/IV ($5 \times 10^9$ amino acid sequence diversity), TN10/IX (having a potential $3 \times 10^{16}$ amino acid sequence diversity), TN12/I (having a potential $4.6 \times 10^{19}$ amino acid sequence diversity). The structure of the variegated templates characterizing each of these libraries has been described above. Each library was diluted into 100 μL of binding buffer (50 mM Tris, 150 mM NaCl, 2 mM $CaCl_2$, 0.05% Tween-20).

Before selecting phage that bound to the fibrin or DD(E) targets, at the beginning of each screening round, the libraries were depleted of most fibrinogen binders: Fibrinogen was biotinylated by the same method employed for DD(E) biotinylation, and immobilized on magnetic beads. The beads were aliquoted into five tubes. The phage library was incubated with the beads in the first tube for 10 minutes, the beads were pelleted with a magnet, and the supernatant, now at least partially depleted of fibrinogen binding phage, was transferred to a second tube. This process was repeated over the five tubes, and after the last depletion, the library was introduced to the microtiter plates containing the immobilized DD(E) target, prepared as above. After a 2-hour incubation with the target to allow binding of phage to DD(E), the wells of the plate were washed extensively (15 times) to remove unbound or weakly bound phage. Bound phage were recovered by eluting the phage from the target in pH 2.0 citrate buffer (10 mM citrate, 150 mM NaCl). The recovered phage were propagated and prepared for use in the succeeding round of selection. In all, five rounds of depletion and selection were conducted. After each round, the phage eluted were counted to determine if the amount of phage recovered (as a percent of the input) increased, an indication that the screening process was converging on a small family of sequences.

Example 3

Discovery of Fibrinogen Binding Polypeptides

After five rounds of selection, the eluted and non-eluted fibrin-binding phage were propagated and a portion plated to isolate phage plaques arising from individual clones. Clones were selected methodically, propagated, and tested individually for binding to fibrin in a dried fibrin plate assay. Dried fibrin plates were prepared as described above for the library screening. Phage samples (~$10^9$ phage each) were incubated in the dried fibrin plate wells in binding buffer (50 mM Tris, 150 mM NaCl, 2 mM $CaCl_2$, 0.05% Tween-20) containing 0.1% HSA. After 1 hour, the plates were washed 5 times with binding buffer. Anti-M13 antibody conjugated to horseradish peroxidase (Pharmacia) was added at 1/5000 dilution in binding buffer to the wells and incubated with the fibrin for 1 hour. The wells were again washed 5 times with binding buffer and the presence of the antibody/phage/fibrin complex was measured with HRP calorimetric reagents (3,3',5,5'-tetramethylbenzidine (TMB) and $H_2O_2$). A high absorbance at 595 nm (due to oxidized TMB) was indicative of a tight phage/fibrin interaction, and phage clones corresponding to those wells were identified as bearing fibrin-binding moieties.

To select for fibrinogen binding, another selection was conducted using biotinylated fibrinogen and streptavidin-coated 96-well microtitre plates, following the procedures described above. As in the previous ELISA, all incubations were done in binding buffer. Several positive isolates were identified from ELISA work following the procedures described above. A non-binding M13 phage not exhibiting any display peptide was used as a control.

The majority of clones tested were fibrin binders that did not bind fibrinogen. However, several phage isolates displayed polypeptides having an affinity for a fibrinogen target.

DNA from isolated phage displaying fibrinogen binding polypeptides may be isolated and sequenced using any of the various standard M13 DNA sequencing protocols available in the art (see, e.g., U.S. Pat. No. 5,223,409 and Kay et al., supra), including various commercially available sequencing kits. For sequencing DNA encoding peptides displayed on the particular phage isolates described here, a commercially available kit for polymerase chain reaction (PCR) sequencing of M13 phage was used (TWO BIG DYE™, Applied Biosystems, Foster City, Calif.). Briefly, overnight phage cultures were diluted 100-fold with distilled water and amplified by PCR using 3PCRUP and 3PCRDN primers. The amplified products were then diluted 1:20 with twice distilled water, and 3 µl aliquots of the PCR amplified nucleic acid products were sequenced basically following the manufacturer's suggested procedure. The sequence reactions were set up in 10 µl volumes using the PCRB3DN and 3Seq-80 primer molecules. The sequencing reaction products were run on an automated Applied Biosystems 3700 fluorescence sequencing machine and sequence data collected.

The amino acid sequences of the phage-displayed fibrinogen polypeptides were deduced from the DNA sequencing data. The amino acid sequences are set forth in Table 1, below.

TABLE 1

Fibrinogen Binding Polypeptides Isolated by Phage ELISA

| Library | Amino Acid Sequence | SEQ ID NO: |
|---------|---------------------|------------|
| TN6/VI  | YWYCDSWHCGVF        | 33         |
|         | HWYCTWHGCVHW        | 34         |
| TN7/IV  | LPQCEMYGTCWTY       | 35         |
|         | DGWCKPPLWCWQL       | 36         |
| TN8/IX  | YWWCAVWGEQCVTR      | 37         |
|         | VPSCMVMDMWCPWN      | 38         |
| TN9/IV  | WVPCDPTWLYCWST*     | 39         |
|         | WLPCADNRWLLCFFG     | 40         |
|         | PLVCVESPNYHCIVL     | 41         |
|         | PNHCHAAYKPGCWHS     | 42         |
| TN10/IX | LYLCNSYPMHPYCNPS    | 43         |
|         | FDYCSANTYSLYCHFF    | 44         |
|         | HWLCMSRWIAYWCVDN    | 45         |
| TN12/I  | GSSCSWVKVGWLWECADD  | 46         |

*During the course of DNA synthesis, there is always a small percentage of incomplete couplings at each cycle. Since the libraries used were constructed by coupling trinucleotides (codons) instead of single nucleotides, the library template DNA often has a small percentage of deleted codons. In the case of the isolate sequence marked with an asterisk(*), binding phage displaying a shorter polypeptide than the template design were present in the library and were isolated when exposed to the fibrinogen target.

Once phage isolate DNA sequences were determined, corresponding peptides were commercially synthesized by solid phase synthesis using standard 9-fluorenylmethoxycarbonyl (FMOC) protocols (Bachem Bioscience, King of Prussia, Pa.) and were purified by reverse-phase chromatography. Masses were confirmed by electrospray mass spectrometry, and peptides were quantified by ultraviolet absorbance at 280 nm. Unvaried phage-derived dipeptides at the N-terminus (i.e., Gly-Ser-, Ala-Gly-, Gly-Asp-) and the C-terminus (i.e., -Ala-Pro, -Gly-Thr, -Asp-Pro) flanking each selected amino acid sequence were retained, and each synthesized polypeptide was N-terminally acetylated. Also, a -Gly-Gly-Gly-Lys-$NH_2$ (SEQ ID NO:47) amidated carboxy-terminal linker was added to the C-terminus of each peptide. For those peptides with internal lysine residues, the internal lysine was protected with 1-(4,4-dimethyl-2,6-dioxocyclohex-1-ylidene)-3-methylbutyl (ivDde) (Chan, *Tetrahedron Lett.*, 39: 1603–1606 (1998)). This protecting group allows selective coupling on the C-terminal lysine, is not removed during peptide cleavage, and can be removed after derivatization on the C-terminal lysine using 2% hydrazine in dimethylformamide (DMF) or 0.5 M hydroxylamine, pH 8.

An apparent dissociation constant was determined for a selected polypeptide. For this determination, the polypeptide was labeled on the C-terminal end with NHS-fluorescein. Fluorescence anisotropy measurements were performed in 384-well microplates in a volume of 10 µl in binding buffer using a Tecan Polarion fluorescence polarization plate reader. The concentration of fluorescein labeled peptide was held constant (20 nM), and the concentration of fibrinogen was varied. The polypeptide was tested in the same binding buffer as used in the selection. The binding mixture was equilibrated for 10 minutes in the microplate at 30° C. prior to performing the measurement. The observed change in anisotropy was fit to the equation below via nonlinear regression to obtain the apparent $K_D$. This equation assumes that the polypeptide and fibrinogen form a reversible complex with 1:1 stoichiometry.

$$r_{obs} = r_{free} + (r_{bound} - r_{free}) \frac{(K_D + Fgn + P) - \sqrt{(K_D + Fgn + P)^2 - 4 \cdot Fgn \cdot P}}{2 \cdot P}$$

where $r_{obs}$ is the observed anisotropy, $r_{free}$ is the anisotropy of the free peptide, $r_{bound}$ is the anisotropy of the bound peptide, $K_D$ is the apparent dissociation constant, Fgn is the total fibrinogen concentration, and P is the total fluorescein-labeled peptide concentration.

The polypeptide based on the TN10/IX polypeptide of SEQ ID NO:43, was a high affinity fibrinogen binder, exhibiting an apparent $K_D$ of 2.0 μM.

Example 4

Peptide Immobilization on NHS-Sepharose Resin

An additional fibrinogen binding polypeptide, containing the cyclic core peptide of SEQ ID NO: 43, was synthesized for further testing:

(SEQ ID NO:48)
Ac-Ala-Glu-Gly-Thr-Gly-Ser-Leu-Tyr-Leu-Cys-Asn-Ser-Tyr-Pro-Met-His-Pro-Tyr-Cys-Asn-Pro-Gly-Lys-NH₂, where Ac— denotes acetylation and —NH2 denotes amidation. Five micromoles of polypeptide SEQ ID NO:48 were dissolved in DMSO in a minimal volume and then added to 1 ml of NHS-sepharose affinity chromatography resin (Amersham Pharmacia Biotech, Piscataway, N.J.), which had been washed once with dimethyl sulfoxide (DMSO). The immobilization reaction was initiated by the addition of diisopropylethylamine to 2% (vol/vol). After 4 hours of slow mixing on a shaker table at room temperature, the reaction was quenched by the addition of an equal volume of 0.5 M hydroxylamine, pH 8, in water. For those peptides with ivDde-protected internal lysines, the hydroxylamine quench treatment also removed the ivDde-protecting group. To allow for complete protecting group removal, the quenched reaction was allowed to incubate overnight at room temperature. Once quenched and deprotected, the immobilized peptide-Sepharose resin was washed at least 3 times with water to remove solvent and unbound peptide. Non-specifically bound peptide was eluted off the resin by washing the resin at least three times in 30 mM phosphoric acid, pH 2. Since the NHS-sepharose resin surface becomes negatively charged after hydrolysis, an acidic wash neutralizes the surface and removes any peptides bound non-covalently to the surface via electrostatic interactions. After washing, the resin was resuspended in water as a 50% v/v mixture. A 50 μl aliquot was used to determine the ligand density on the resin by quantitative amino acid analysis. Finally, the resin slurry was packed into 0.35 ml OMNIFIT™ glass columns (3 mm×50 mm) for analytical testing.

The ligand density of the fibrinogen binding column was about 1 μM/ml. Commercially available human fibrinogen protein (American Diagnostica, Inc., Greenwich, Conn.) was dissolved in TBS, 0.01% Tween-20 at 1 mg/ml concentration and loaded onto the column, which was previously equilibrated in the same buffer. The protein was eluted with 100 mM CAPS, pH 11.5 and neutralized with a ½ volume of 500 mM Tris, pH 8. This elution condition quantitatively removed all bound fibrinogen as determined by comparing the peak areas to the same test injection done onto a hydrolyzed NHS/FF column with no peptide. The column was able to capture (bind) 84% of the fibrinogen in solution.

Example 5

Additional Fibrinogen Binding Column Testing

Two additional columns (0.85 ml OMNIFIT™) having a fibrinogen binding ligand density of 2.0 and 4.0 μM/ml resin were prepared by immobilizing the polypeptide (SEQ ID NO: 48) on NHS-activated Sepharose 4 Fast Flow resin. The polypeptide was completely dissolved in (2×) coupling buffer (200 mM KH₂PO₄, 300 mM NaCl, 0.1% Tween-20, pH 7.5) to 8.2 mg/ml and 1.5 ml of this solution was reacted with 1.5 ml of 1 mM HCl washed media. The reactions were allowed to tumble at room temperature for 3 hours where an aliquot was removed for rp-HPLC analysis. The reaction was then allowed to tumble overnight to completely react and hydrolyze any unreacted NHS-groups. The following morning (~20 hours) the media was sequentially washed with deionized H₂O, 500 mM hydroxylamine-HCl, pH 8.5, dH₂O, 0.1M acetate, 1M NaCl, pH 4.0, dH₂O, 0.1M glycine, pH 2.5, dH₂O and stored in PBS, 20% EtOH, pH 7.2. A control resin, in which all reactive sites were blocked by ethanolamine, was prepared to determine the efficiency of the coupling and to assess the stability of the peptide under the coupling procedure. Coupling efficiency was monitored by HPLC analysis of the reaction sample supernatant as a function of time. After 4 hours, more than 99% of the polypeptide was bound out of solution for the 2.0 μM/ml resin, and more than 94% of the polypeptide was bound out of solution for the 4.0 μM/ml resin.

Figure 2:
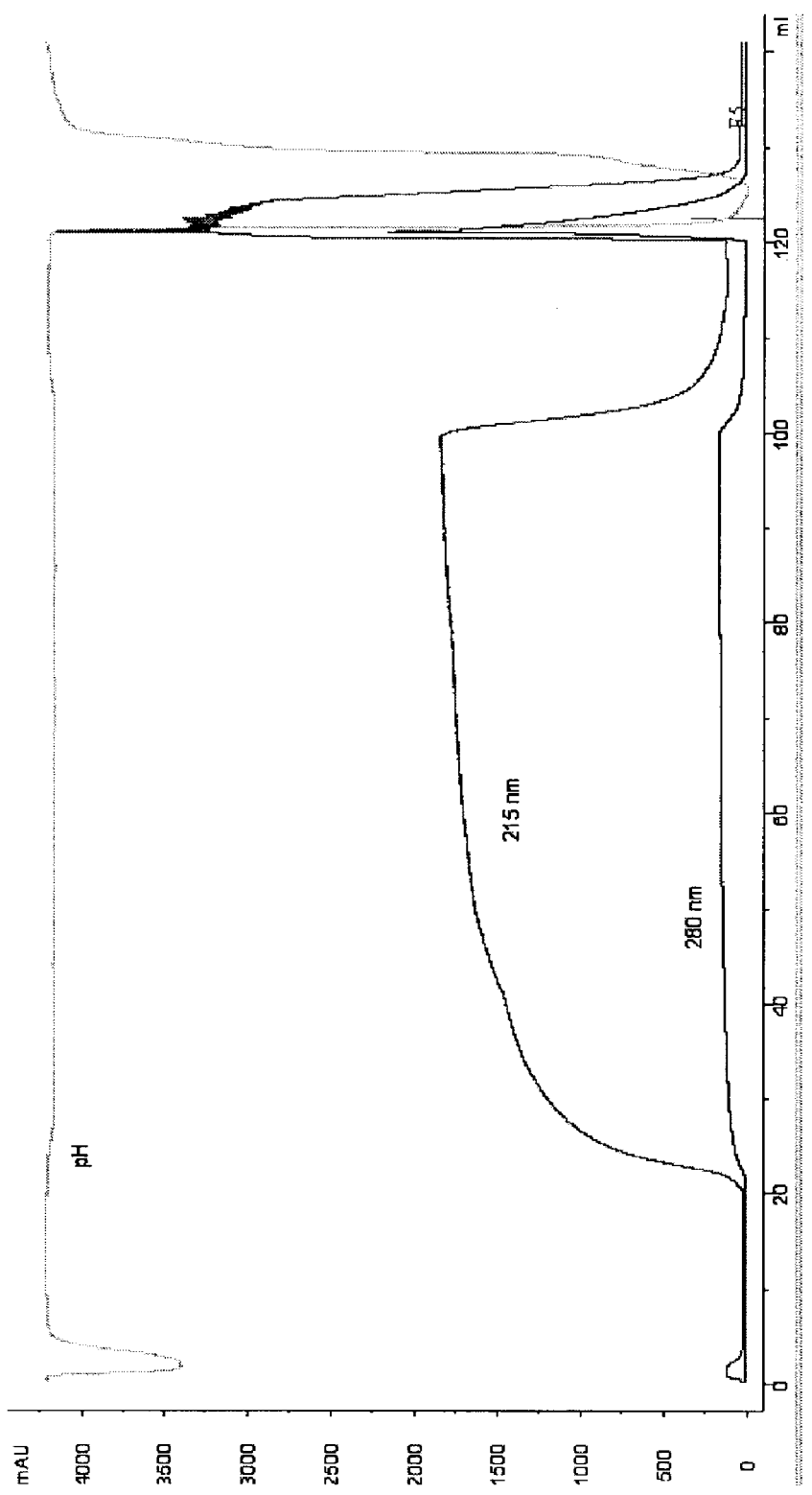
FIG. 2 is a chromatogram illustrating the purified fibrinogen binding capacity of a fibrinogen binding column utilizing the fibrinogen binding peptide of SEQ ID NO:48 and having a ligand density of 4.0 µM/ml resin. Purified fibrinogen (0.5 mg/ml in PBS) was injected continuously onto the column until the A280 reading reached a plateau. The column was then washed with PBS until a baseline reading was obtained and then eluted with glycine buffer (0.1M, pH 2.5). The eluted fraction (major peak) was collected and analyzed by HPLC Size Exclusion Chromatography (SEC). The capacity of the column was calculated to be 4.1 mg fibrinogen/ml resin.

Two columns were prepared (one containing the 2.0 μM polypeptide/ml resin slurry and the other containing the 4.0 μM polypeptide/ml resin slurry). The columns were then analyzed for their ability to bind purified fibrinogen. The capacity of each column was estimated by continuous injection of purified human fibrinogen (Calbiochem, Cat. No. 341576). After column washing, the bound fibrinogen was eluted (FIGS. 1 and 2) and analyzed by SEC HPLC. The 2.0 μM/ml resin column exhibited a fibrinogen binding capacity of 2.076 mg fibrinogen/ml resin. Similarly, the 4.0 μM/ml resin column exhibited a fibrinogen binding capacity of 4.1 mg fibrinogen/ml resin.

Figure 3:
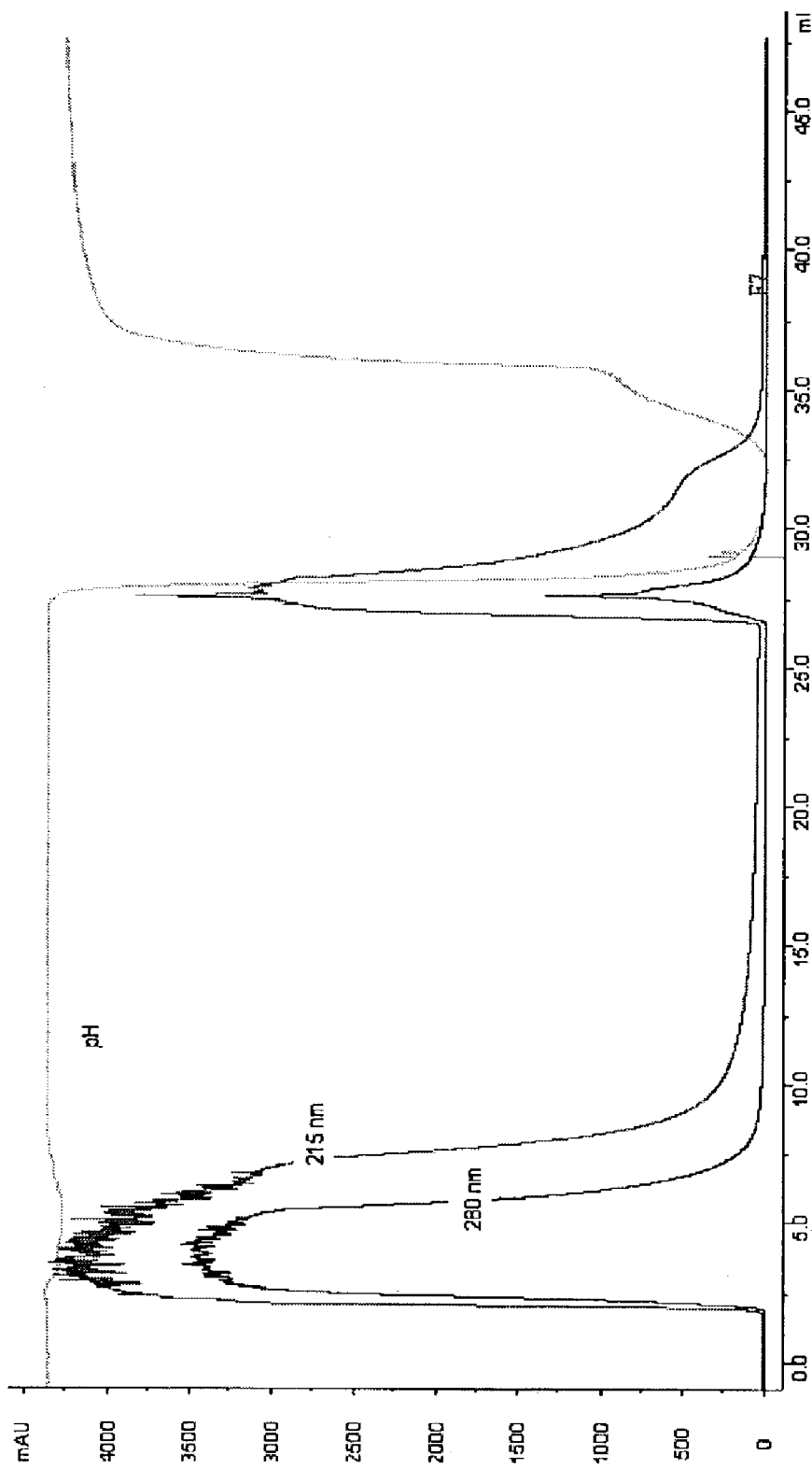
FIG. 3 is a chromatogram illustrating the capacity of the 2.0 µM fibrinogen binding polypeptide/ml resin column (Example 5) to bind fibrinogen in its physiological environment. 10 mls of human plasma was applied to the column at a flow rated of 0.2 ml/min. The column was washed with PBS and then eluted with glycine buffer (0.1M, pH 2.5). The eluted protein was collected and analyzed by SEC HPLC and SDS-PAGE.
Figure 4:
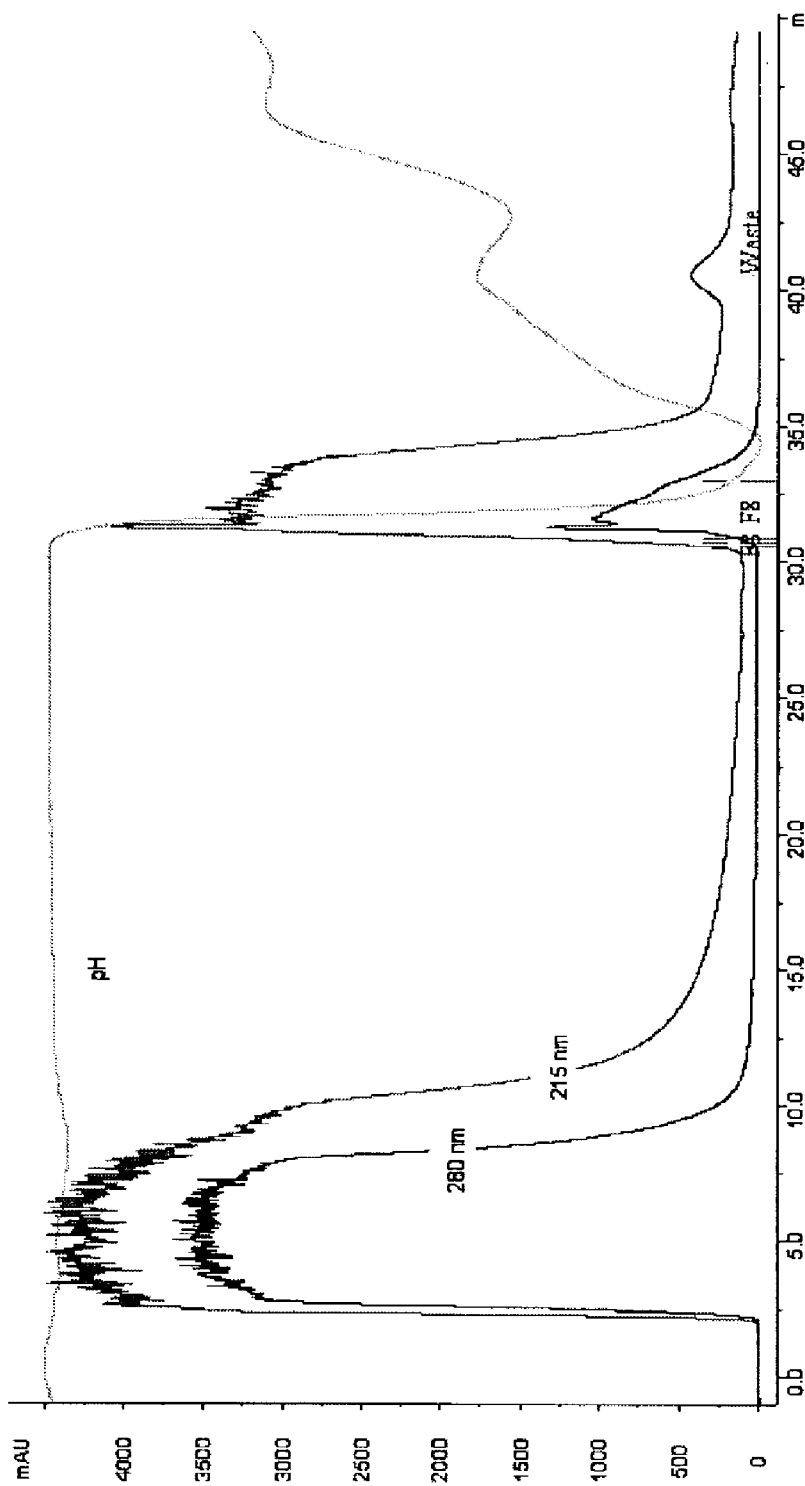
FIG. 4 is a chromatogram illustrating the capacity of the 4.0 µM fibrinogen binding polypeptide/ml resin column (Example 5) to bind fibrinogen in its physiological environment. 10 mls of human plasma was applied to the column at a flow rated of 0.2 ml/min. The column was washed with PBS and then eluted with glycine buffer (0.1M, pH 2.5). The eluted protein was collected and analyzed by SEC HPLC and SDS-PAGE.
Figure 5:
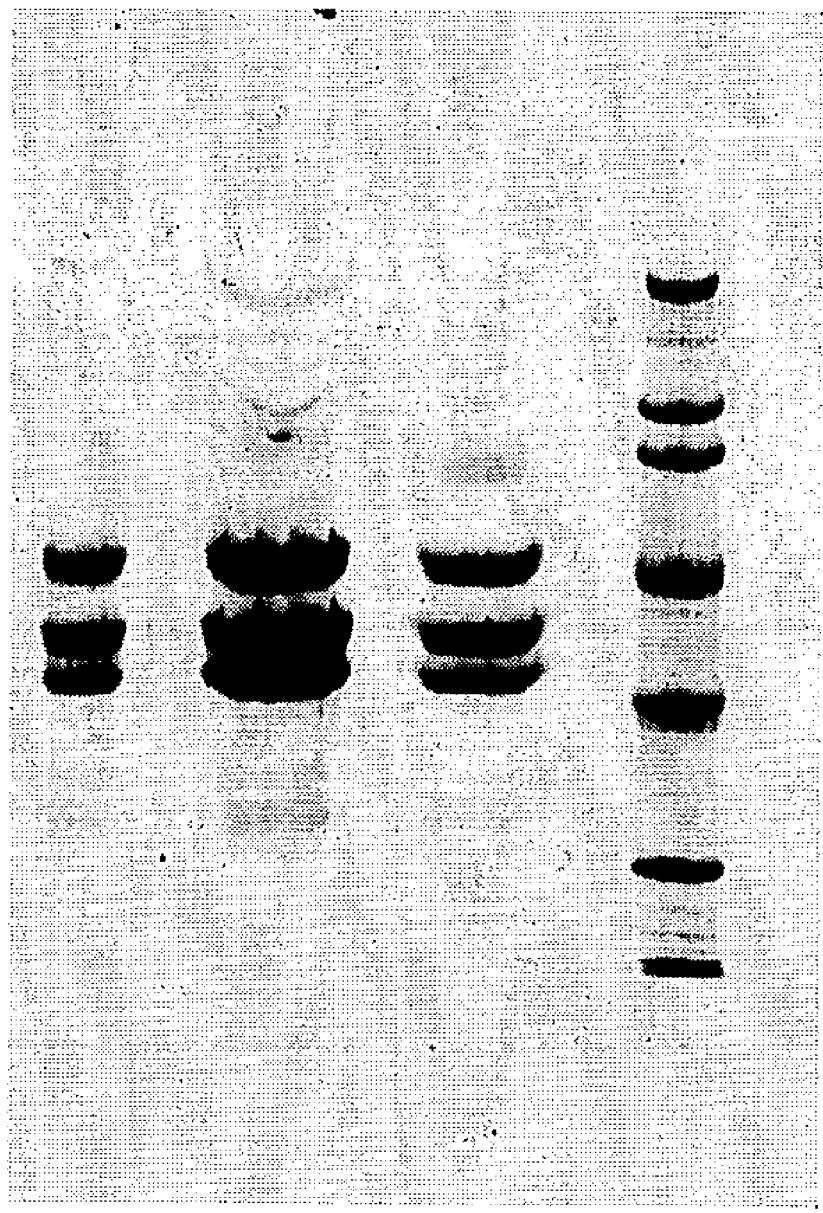
FIG. 5 is a SDS-PAGE photograph showing the profile of the retained proteins from the 4.0 µM polypeptide/ml resin column (Example 5). Lane (A) illustrates the migration of standard purified fibrinogen, lane (B) 5 µg of eluted protein from the column, lane (C) 1 µg of eluted protein from the column, lane (D) molecular weight markers from top to bottom in kDa: 200, 116, 91, 67, 41, 31, 21, 14.

Additionally, the columns were analyzed for their ability to bind fibrinogen in its physiological environment. A fixed volume of human plasma was passed through each column, and the columns were washed with PBS buffer until the A280 absorbance values reached baseline. The retained protein was then eluted using an elution buffer of 100 mM glycine, pH 2.5. (FIGS. 3 and 4). The eluted proteins were collected and analyzed by SEC HPLC and SDS PAGE (FIG. 5). The columns were regenerated using a 50 mM glycine pH 2.5 8M Urea buffer and the injection was repeated several times, with the 2.0 µM/ml resin column consistently binding 1–2 mg of protein per ml of resin and the 4.0 µM/ml resin column consistently binding 3.3–4.0 mg protein per ml resin. The consistent chromatograms and protein recovery illustrate the columns robustness and regenerability, demonstrating that the fibrinogen binding media was regenerable and reusable.

SDS PAGE analysis of the retained proteins in both columns resulted in the presence of three predominant bands, each corresponding in molecular weight to the three known fibrinogen isoforms α(67 kDa), β(52 kDa) and γ(46.5 kDa), which also co-migrated with standard commercial fibrinogen (see FIG. 5). 2D gel electrophoresis and mass spectrometric analysis of the retained fractions was further employed to positively identify the retained protein as fibrinogen (data not shown). The foregoing examples illustrate new, non-natural, isolated peptides that bind mammalian fibrinogen, with micromolar affinity. Once immobilized on a chromatography resin, representative fibrinogen binding peptides of the invention are capable of binding and releasing fibrinogen under gentle elution conditions. A sepharose affinity resin utilizing the fibrinogen binding peptide of SEQ ID NO: 48, in particular, captures fibrinogen effectively out of solutions containing it. Additional embodiments employing fibrinogen binding polypeptides described above will be apparent to those skilled in the art. All such additional embodiments are encompassed by the present invention.

The patents and publications mentioned above are incorporated herein by reference.

We claim:

1. A fibrinogen binding moiety comprising a polypeptide comprising an amino acid sequence of the formula:

Cys-Xaa$_2$-Xaa$_3$-Xaa$_4$-Xaa$_5$-Xaa$_6$-Xaa$_7$-Xaa$_8$-Xaa$_9$-Cys,  (SEQ ID NO:21)

wherein: Xaa$_2$ is Asn, Met, or Ser; Xaa$_3$ is Ala or Ser; Xaa$_4$ is Arg, Asn, or Tyr; Xaa$_5$ is Pro, Thr, or Trp; Xaa$_6$ is Ile, Met, or Tyr; Xaa$_7$ is Ala, His, or Ser; Xaa$_8$ is Leu, Pro, or Tyr; and Xaa$_9$ is Trp or Tyr.

2. The binding moiety according to claim 1, wherein said polypeptide comprises an amino acid sequence selected from the group consisting of:

Gly-Ser-Leu-Tyr-Leu-Cys-Asn-Ser-Tyr-Pro-Met-His-Pro-Tyr-Cys-Asn-Pro-Ser-Ala-Pro,  (SEQ ID NO:22)

Gly-Ser-Phe-Asp-Tyr-Cys-Ser-Ala-Asn-Thr-Tyr-Ser-Leu-Tyr-Cys-His-Phe-Phe-Ala-Pro,  (SEQ ID NO:23)

Gly-Ser-His-Trp-Leu-Cys-Met-Ser-Arg-Trp-Ile-Ala-Tyr-Trp-Cys-Val-Asp-Asn-Ala-Pro.  (SEQ ID NO:24)

3. The binding moiety according to claim 1, wherein said polypeptide comprises an amino acid sequence of the formula:

Ac-AEGTGSLYLCNSYPMHPYCNPGK-NH$_2$  (SEQ ID NO:48)

where Ac— denotes acetylation and —NH$_2$ denotes amidation.

4. A fibrinogen binding moiety according to any one of claims 1 or 3, wherein said polypeptide is expressed by a recombinant bacteriophage.

5. A composition of matter comprising a binding moiety according to any one of claims 1 or 3 linked to a solid support material selected from the group consisting of cellulose, plastic, metal, rubber, wood, nylon, glass, acrylamide, agarose, and combinations thereof.

6. The composition according to claim 4, wherein said binding moiety is linked to a chromatographic matrix material.

7. A composition, of matter comprising a binding moiety according to any one of claims 1 or 3 linked to a detectable label.

8. The composition according to claim 7, wherein said detectable label is selected from the group consisting of radionuclides, detectable proteins, epitope tags, biotin, streptavidin, enzymes, antibodies, and fluorescent labels.

9. The composition according to claim 8, wherein the detectable label is a technetium-containing compound.

10. A composition of matter comprising a binding moiety according to any one of claims 1 or 3 linked to a drug, biopharmaceutical, or polypeptide of interest.

11. A method for detecting fibrinogen in a solution comprising: (a) contacting said solution with a binding moiety according to any one of claims 1 or 3 under conditions wherein said binding moiety will form a complex with said fibrinogen, and (b) detecting said complex.

12. The method according to claim 11, wherein the solution is blood and the binding moiety is linked to a detectable label.

13. A method for isolating fibrinogen from a solution containing it comprising: (a) immobilizing a composition according to any one of claims 1 or 3 on a solid support; (b) contacting a solution containing fibrinogen with said solid support of (a) under conditions wherein said binding moiety will form a complex with said fibrinogen; and, thereafter, (c) separating the solid support from the unbound components of said solution.

14. The method according to claim 13, wherein said solid support is selected from the group consisting of chromatographic matrix materials, filters, magnetic beads, and the surface of a plastic or glass container.

15. The method according to claim 13, further comprising the step: (d) eluting and recovering the fibrinogen from said support.

16. The method according to claim 15, wherein the eluant used in step (d) is a citrate buffer or a glycine buffer.

17. The method according to claim 13, wherein the solution is selected from the group consisting of a recombinant eukaryotic or prokaryotic cell extract, and whole blood.

18. A method for isolating fibrinogen from a solution containing it comprising: (a) contacting a solution containing fibrinogen with a binding moiety according to any one of claims 1 or 3, in which said binding moiety is conjugated to an affinity ligand, under conditions suitable for formation of a binding complex between said binding moiety and said fibrinogen; (b) contacting the solution of step (a) with an immobilized binding partner for said affinity ligand under conditions suitable for formation of a binding complex between the affinity ligand and the binding partner; and (c) removing unbound materials in the solution from the complex formed in step (b).

19. The method according to claim 18, wherein said affinity ligand is a polyhistidine tag.

20. The method according to claim 18, wherein said affinity ligand is biotin and said immobilized binding partner for said affinity ligand is streptavidin.

21. A method for assessing blood circulation in a subject comprising: (a) introducing into the circulatory system of the subject a composition comprising a detectable binding moiety according to claim 7, and (b) detecting any circulation of complexes formed between said detectable binding moiety and fibrinogen in the circulatory system of said subject.

22. The method according to claim 21, wherein said detectable compound consists essentially of a complex of said detectably labeled binding moiety and fibrinogen.

23. The method according to claim 21, wherein the binding moiety is detectably labeled with a magnetic resonance imaging agent.

* * * * *

UNITED STATES PATENT AND TRADEMARK OFFICE
CERTIFICATE OF CORRECTION

PATENT NO. : 7,041,790 B2 Page 1 of 1
APPLICATION NO. : 10/396073
DATED : May 9, 2006
INVENTOR(S) : Charles R. Westcott and Aaron K. Sato It is certified that error appears in the above-identified patent and that said Letters Patent is hereby corrected as shown below:

Column 57, lines 42, 58, 60, and 62 replace "[_____]" with -- |—————|-- there are 4 occurrences.

Signed and Sealed this

Tenth Day of April, 2007

JON W. DUDAS
*Director of the United States Patent and Trademark Office*